(12) United States Patent
Shukla

(10) Patent No.: US 10,588,825 B1
(45) Date of Patent: *Mar. 17, 2020

(54) PILL COMPLIANCE DEVICE AND MONITORING SYSTEM

(71) Applicants: Manan Shukla, Roslyn Heights, NY (US); Mayank Shukla, Roslyn Heights, NY (US)

(72) Inventor: Manan Shukla, Roslyn Heights, NY (US)

(73) Assignees: Manan Shukla, Roslyn Heights, NY (US); Mayank Shukla, Roslyn Heights, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/218,426

(22) Filed: Dec. 12, 2018

Related U.S. Application Data

(63) Continuation-in-part of application No. 15/952,972, filed on Apr. 13, 2018.

(Continued)

(51) Int. Cl.
  *G08B 1/08* (2006.01)
  *A61J 7/04* (2006.01)
  (Continued)

(52) U.S. Cl.
  CPC ............... *A61J 7/0436* (2015.05); *A61J 1/03* (2013.01); *G16H 20/13* (2018.01); *A61J 2200/30* (2013.01)

(58) Field of Classification Search
  CPC ........ A61J 7/0436; G16H 230/13; A61B 5/00
  (Continued)

(56) References Cited

U.S. PATENT DOCUMENTS

| 7,081,807 B2 | 7/2006 | Lai |
| 8,754,769 B2 * | 6/2014 | Stein ..................... A61J 7/0409 340/540 |

(Continued)

FOREIGN PATENT DOCUMENTS

WO 2013127564 A1 9/2013

OTHER PUBLICATIONS

L. Lorenc, A. Branthwaite; "Are Older Adults Less Compliant with Prescribed Medication than Younger Adults?"; https://www.ncbi.nlm.nih.gov/pubmed/8298546; Nov. 1993; Abstract.

(Continued)

*Primary Examiner* — Tai T Nguyen
(74) *Attorney, Agent, or Firm* — Alfred M. Walker; John F. Vodopia

(57) ABSTRACT

A pill compliance device maintains a patient's pill supply and monitors the patient's access to pills contained in the device to memorialize the patient's compliance with his/her pill-taking regimen. The device has a housing, including an inner pill or capsule storage compartment and an electronics unit, a removable cover, a switch to detect removal of the cover and magnet away from the housing, and to detect a replacement of the cover and magnet to the housing, wherein activating the switch triggers a transition from an active state, to a dormant state, and vice versa. A transition from the dormant state to the active state, by replacing the cover to the housing generates a pill-taken signal. A microcontroller generates a compliance notification signal that is communicated to a Wi-Fi module or router within or attached to the electronics unit, to memorialize the apparent compliance.

21 Claims, 13 Drawing Sheets

Related U.S. Application Data

(60) Provisional application No. 62/485,730, filed on Apr. 14, 2017.

(51) Int. Cl.
   *A61J 1/03* (2006.01)
   *G16H 20/13* (2018.01)

(58) Field of Classification Search
   USPC .................. 340/539.1, 309.16, 531; 600/300
   See application file for complete search history.

(56) References Cited

U.S. PATENT DOCUMENTS

| | | | |
|---|---|---|---|
| 9,579,264 B1 | 2/2017 | Litton | |
| 10,071,023 B2 | 9/2018 | Stein et al. | |
| 10,073,954 B2 | 9/2018 | Chen et al. | |
| 10,091,468 B2 | 10/2018 | Mehrotra et al. | |
| 10,445,472 B2* | 10/2019 | LeBrun | G16H 40/63 |
| 2006/0139150 A1* | 6/2006 | Brue | A61J 7/0481 340/309.16 |
| 2010/0270257 A1 | 10/2010 | Wachman | |
| 2013/0222135 A1 | 8/2013 | Stein et al. | |
| 2016/0048657 A1* | 2/2016 | LeBrun | G06F 19/3462 705/2 |
| 2016/0324726 A1 | 11/2016 | Roberts et al. | |

OTHER PUBLICATIONS

V. Senior, TM Marteau, J Weinman; "Genetic Risk Assessment for FH Trial (GRAFT) Study Group"; 'Self-reported adherence to cholesterol-lowering medication in patients with familial hypercholesterolaemia: the role of illness perceptions'; Psychology and Genetics Research Group, Guy's Medical School, King's College London, UK; https//www.ncbi.nlm.nih.gov/pubmed/15770435; Nov. 2004; Abstract.
MC Sokol, KA McGuigan, RR Verbrugge, RS Epstein; "Impact of Medication Adherence on Hospitalization Risk and Healthcare Cost"; Dept. of Medical Affairs, Medco Health Solutions, Franklin Lakes, NJ; https://www.ncbi.nlm.nih.gov/pubmed/15908846; Abstract.
Lars Osterberg, MD, Terrence Blaschke, MD; "Adherence to Medication"; The New England Journal of Medicine; Aug. 4, 2005; 353:487-497.
Alex J. Mitchell, Thomas Selmes; "Why Don't Patients Take Their Medicine? Reasons and Solutions in Psychiatry"; The Royal College of Psychiatrists 2006, Cambridge Core; Sep. 2007; vol. 13, Issue 5.
Me Inkster, PT Donnan, TM MacDonald, FM Sullivan, T Fahey; "Research Letter: Adherence to antihypertensive medication and association with patient and practice factors"; Journal of Human Hypertension (2006) 20-295-297; published on line Jan. 19, 2006.
Jeffrey K Aronson; "Compliance, Concordance, Adherence"; British Journal of Clinical Pharmacology; Apr. 2007; www.ncbi.nlm.nih.gov/pmc/articles/PMC2203247, 383-384.
AK Jha, EJ Oray, A Dobson, RA Book, AM Epstein; "Measuring Efficiency: the Association of Hospital Costs and Quality of Care"; Health Aff (Millwood); May-Jun. 2009; pp. 897-906.
Michael A Rapoff; "Adherence to Pediatric Medical Regimens", 'Consequences of Nonadherence and Correlates of Adherence'; Springer; 2010, pp. 33-45.
Hayden B Bosworth; "Medication Adherence"; 'Improving Patient Treatment Adherence'; Springer; 2019; pp. 68-94.
Roundtable: PL Yong, RS Saunders, LA Olsen; The Healthcare Imperative: Lowering Costs and Improving Outcomes:Workshop Series Summary; Institute of Medicine (US) Roundtable on Evidence Based Medicine; 2010; www.ncbi.nlm.nih.gov/pubmed/21595114.
Roundtable: Joint Workshop; Emerging Threat of Drug-Resistant Tuberculosis in Southern Africa; Institute of Medicine (US) Forum on Drug Discovery, Development, and Translation; Academy of Science of South Africa; National Academies Press (US) 2011; https://www.ncbi.nlm.nih.gov/books/NBK55582.
Marie T Brown, MD, Jennifer K Bussell, MD; "Medication Adherence: WHO Cares?"; Mayo Clinic Proceedings; Apr. 2011; https://www.ncbi.nlm.nih.gov/pmc/articles/PMC3068890, pp. 304-314.
Pharmacist Case Study: "Adherence to Oral Antidiabetic Medication and Glycemic Control"; Prime(R) Clinical Case Study; Feb. 2, 2012; https://primeinc.org/casestudies/pharmacist/study/725.
Donald M. Berwick, MD, MPP, Andrew D. Hackbarth, MPhil; "Eliminating Waste in US Health Care"; JAMA, Apr. 11, 2012; https://jamanetwork.com/journals/jama/article-abstract/1148376.
Brian Fung; "How the US Health-Care System Wastes $750 Billion Annually"; The Atlantic; Sep. 7, 2012; https://www.theatlantic.com/health/archive/2012/09/how-the-us-health-care-system-wastes-750-billion-annually/262106.
IMS Institute for Healthcare Informatics; "Avoidable Costs in US Healthcare"; Jun. 2013.
Karl E Friedl, Thomas B Talbot, Steve Steffensen; "Information Science and Technology—A New Paradigm in Military Research"; Chapter 1; Jun. 2013; https://www.researchgate.net/publication/260892371.
EG Devine, ME Waters, M Putnam, C Surprise, K O'Malley, C Richambault, RL Fishman, CM Knapp, EH Patterson, O Sarid-Segal, C Streeter, L Colanari, Da Ciraulo; (Dept. Of Psychiatry, Boston University School of Medicine, Boston, MA); "Concealment and Fabrication by Experienced Research Subjects"; Jul. 2018; https://www.ncbi.nlm.nih.gov/pubmed/238672323.
Aurol O Luga, Maura J McGuire; "Adherence and Health Care Costs"; Risk Management and Healthcare Policy, Dovepress, Feb. 20, 2014; https://www.ncbi.nlm.nih.gov/pmc/articles/PMC 3934668.
Nonika Rajkumari; "Impact of Technology in Better Dispersal of Health Care Methods and Improving Health Care Systems"; Department of Laboratory Medicine (Microbiology Division), Jai Prakash Narayan Apex Trauma Center, All India Institutes of Medical Sciences, New Delhi, India, Occupational Medicine and Health Affairs; May 27, 2014, vol. 2, Issue 3.
B Vrijens, J Urquhart; "Methods for Measuring, Enhancing, and Accounting for Medication Adherence in clinical trials"; Clinical Pharmacol Ther., Jun. 2014 (epub Mar. 12, 2014).
HCL Technologies; "Patient Support/Enablement Programs for Clinical Trial Adherence"; Aug. 26, 2014; https//www.slideshare.net/hcl.
Karen Davis, Kristof Stremikis, David Squires, Cathy Schoen; "Mirror, Mirror on the Wall—How the Performance of the US Health Care System Compares Internationally"; 2014 Update, Executive Summary; The Commonwealth Fund, NY, NY; pp. 1-9.
Michael Crowe, "Do You Know the Difference Between These Adherence Measures?"; Pharmacy Times, Jul. 6, 2015; https://www.pharmacytimes.com/contributor/michael-crowe-pharmd-mba-csp-fmp/2015/07.
Nikhil R. Sahni, Anuraag Chigurupati, Bob Kocher, MD, David M. Cutler; "How the US Can Reduce Waste in Health Care Spending by $1 Trillion"; Harvard Business Review "Economy"; Oct. 13, 2015.
National Center for Health Statistics; "Percent of US Adults 55 and Over with Chronic Conditions"; National Health Interview Survey; National Center For Health Statistics; Nov. 6, 2015.
Centers for Medicare & Medicaid Services; "National Health Expenditure Projections 2015-2025-Forecast Summary"; Centers for Medicare and Medicaid Service, Office of the Actuary; 2015.
Medsignals (R) Pill Case/Monitor; Apr. 8, 2018; http://www.medsignals.com/medsignals-pillcase.
US Census Bureau; "American Community Survey Provides New State and Local Income, Poverty and Health Insurance Statistics"; Sep. 26, 2019; Release No. CB19-152.
E-pill|Medsmart Plus|Monitored Automatic Pill Dispenser; e-pill, LLC, Wellesley, MA; Oct. 2019; https://ww.epill.com/medsmartplus.html.
Hospitals Insurance Company (c) 2019; "Thought: Leadership—What is the Impact of Nonadherence on Public Health and Health Care?"; https://hicgroup.co/publications/what-impact-non-adherence-public-health-and-health-care.

(56) References Cited

OTHER PUBLICATIONS

Gary Becker, Director, "Medication Non-Adherence"; Vimeo, Oct. 3, 2019, vimeo.com/132741644.

* cited by examiner

Medicobox Assembly Process

| Patient Data | | | | |
|---|---|---|---|---|
| File Edit View Insert Format Data Tools Form Add-ons Help | | | | |

7:46:50 PM

| | Timestamp | First Name: | Last Name: | Email: | Phone Number: |
|---|---|---|---|---|---|
| 43 | 10/20/2016 21:43:50 | First Name: | Last Name: | Email: | Phone Number: |
| 44 | 10/20/2016 21:44:38 | First Name: | Last Name: | Email: | Phone Number: |
| 45 | 10/20/2016 21:45:38 | First Name: | Last Name: | Email: | Phone Number: |
| 46 | 10/20/2016 21:52:09 | First Name: | Last Name: | Email: | Phone Number: |
| 47 | 10/20/2016 21:52:10 | First Name: | Last Name: | Email: | Phone Number: |
| 48 | 10/20/2016 21:52:11 | First Name: | Last Name: | Email: | Phone Number: |
| 49 | 10/20/2016 21:52:12 | First Name: | Last Name: | Email: | Phone Number: |
| 50 | 10/20/2016 21:52:18 | First Name: | Last Name: | Email: | Phone Number: |
| 51 | 10/20/2016 21:52:19 | First Name: | Last Name: | Email: | Phone Number: |
| 52 | 10/20/2016 21:52:21 | First Name: | Last Name: | Email: | Phone Number: |
| 53 | 10/20/2016 21:52:22 | First Name: | Last Name: | Email: | Phone Number: |
| 54 | 10/20/2016 21:52:24 | First Name: | Last Name: | Email: | Phone Number: |
| 55 | 10/20/2016 21:52:29 | First Name: | Last Name: | Email: | Phone Number: |
| 56 | 10/20/2016 21:52:30 | First Name: | Last Name: | Email: | Phone Number: |
| 57 | 10/20/2016 21:52:31 | First Name: | Last Name: | Email: | Phone Number: |
| 58 | 10/20/2016 21:52:32 | First Name: | Last Name: | Email: | Phone Number: |
| 59 | 10/20/2016 21:52:33 | First Name: | Last Name: | Email: | Phone Number: |
| 60 | 10/20/2016 21:52:34 | First Name: | Last Name: | Email: | Phone Number: |
| 61 | 10/20/2016 21:52:35 | First Name: | Last Name: | Email: | Phone Number: |
| 62 | 10/20/2016 21:52:37 | First Name: | Last Name: | Email: | Phone Number: |

Fig. 9

```
void setup() {
  //start serial connection
  Serial.begin(9600);
  //configure pin2 as an input and enable the internal pull-up resistor
  pinMode(2, INPUT_PULLUP);
  pinMode(13, OUTPUT);

} void loop() {
  //read the pushbutton value into a variable
  int sensorVal = digitalRead(2);
  //print out the value of the pushbutton
  Serial.printin(sensorVal);

// Keep in mind the pullup means the pushbutton's
  // logic is inverted. It goes HIGH when it's open,
  // and LOW when it's pressed. Turn on pin13 when the
  // button's pressed, and off when it's not;
  if (sensorVal == HIGH) {
    digitalWrite(13, LOW);
    delay(1000);
  } else {
    digitalWrite(13, HIGH);
    delay(1000)'
  }
}
```

*Fig. 10*

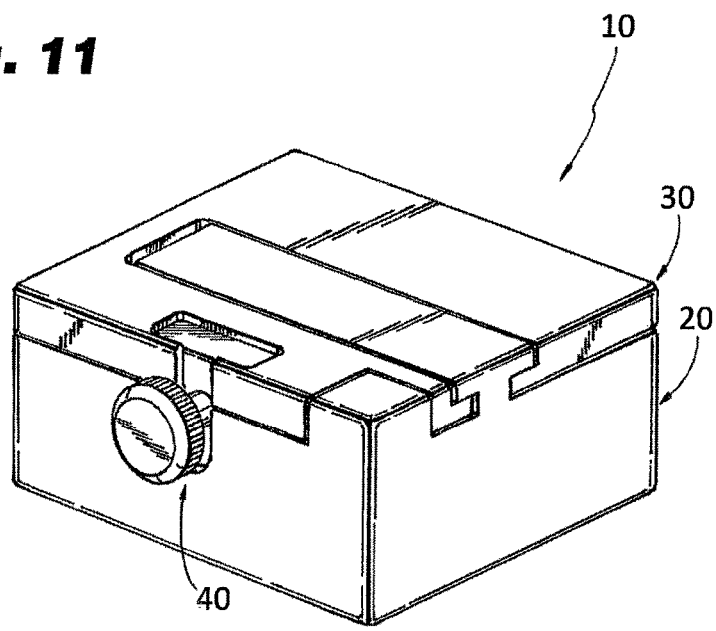
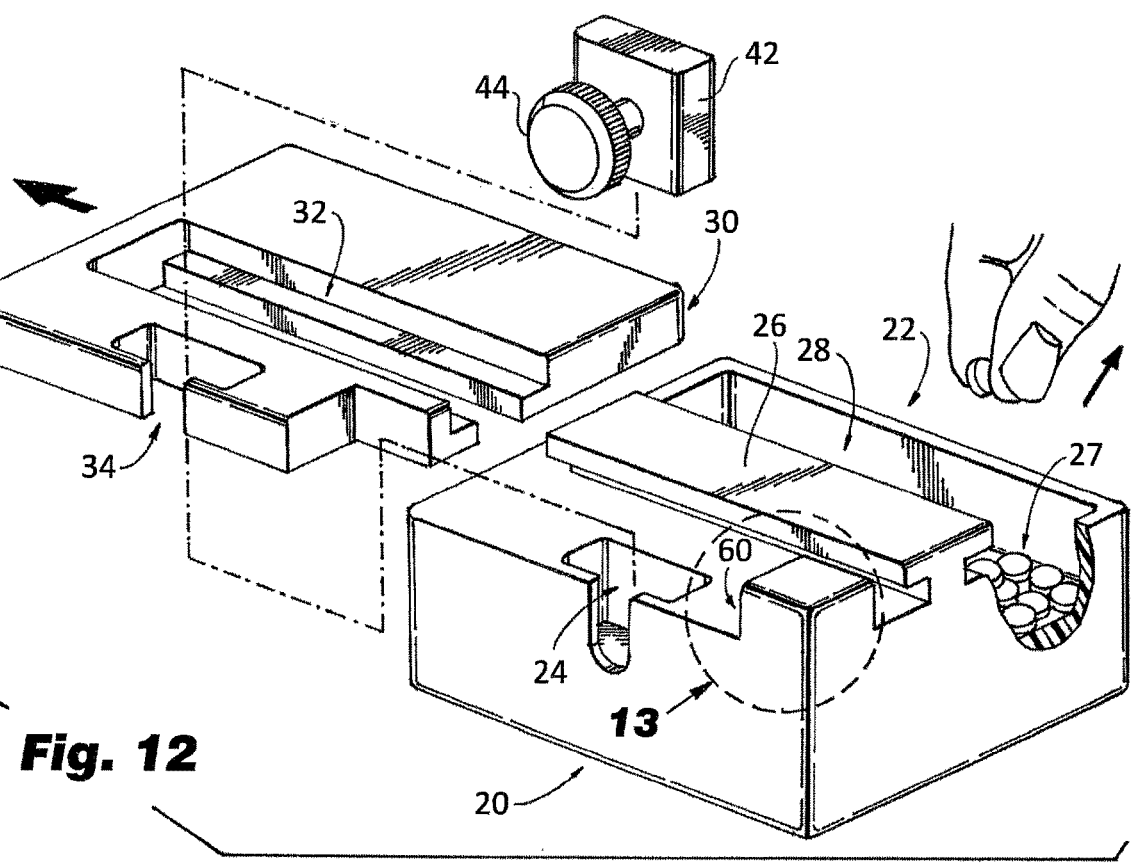

```
// We will be using D1 to control our LED int ledPin = D7;

// Our button wired to D0
int buttonPin = D0;

void setup()
{

// For input, we define the
  // pushbutton as an input-pullup
  // this uses an internal pullup resistor
  // to manage consistent reads from the device pinMode( buttonPin , INPUT_PULLUP); // sets pin as input // We also want to use the LED pinMode( ledPin , OUTPUT ); // sets pin as output

} void loop()
{
  // find out if the button is pushed
  // or not by reading from it.
  int buttonState = digitalRead( buttonPin );

// remember that we have wired the pushbutton to
  // ground and are using a pulldown resistor
  // that means, when the button is pushed,
  // we will get a LOW signal
  // when the button is not pushed we'll get a HIGH // let's use that to set our LED on or off if( buttonState == LOW )
  {
    // turn the LED On
    digitalWrite( ledPin, HIGH);
       Particle.publish("Meds_Taken", NULL, 60, PRIVATE);
       delay (5000);
  }else{
    // otherwise
    // turn the LED Off
    digitalWrite( ledPin, LOW);

… # PILL COMPLIANCE DEVICE AND MONITORING SYSTEM

RELATED APPLICATIONS

This application claims priority in part under 35 U.S.C. § 120 from U.S. patent application Ser. No. 15/952,972 filed on Apr. 13, 2018. The '972 application is incorporated by reference herein. This application also claims benefit under 35 USC § 119 (e) of provisional application No. 62/485,730 filed Apr. 14, 2017. The '730 application is incorporated by reference herein.

FIELD OF THE INVENTION

The present invention relates to dispensing and monitoring adherence to the correct ingestion of prescribed pharmaceutical pills/capsules for a medical patient.

BACKGROUND OF THE INVENTION

The present invention relates to dispensing and monitoring adherence to the correct ingestion of prescribed pharmaceutical pills/capsules for a medical patient. The United States healthcare is at jeopardy, with approximately three trillion dollars spent in 2014, and a projected increase by 5.85% by 2025. Although such tremendous spending occurs, the United States straggles behind all of her first world countries, implying that most of the spending is a waste. Out of the many causes behind such an enormous problem, it is noncompliance that is the most wasteful out of all. Occupying a third of healthcare waste, noncompliance is the origin and root of healthcare waste in the United States. Approximately 290 billion dollars were wasted in this sector in 2012, with a continual rise since. Defined as the degree of impassiveness of a patient in adhering to advice given by a prescriber or doctor, medical noncompliance has surpassed all other crises faced in healthcare today.

There are many reasons and consequences behind medical noncompliance. Reasons behind compliance can include correlations between race, gender, age, in addition to experiencing unwanted side effects, financial issues, etc. Its consequences are drastic, leading to avoidable hospitalization, false results in clinical studies, and decreased efficiency for doctors, pharmacists and other medical personnel.

Although there have been some solutions to such a problem, little is done overall to solve it. Even the most effective technologies in the market, pill bottles, are either too expensive, or do not solve the initial problem of noncompliance. With the creation of a patented device, Medicobox™ pill compliance device is able to efficiently and effectively provide immediate compliance to the patient, doctor, pharmacist and other healthcare providers. In addition, it provides a reminder system to limit unintentional compliance such as forgetfulness. This is incredibly beneficial to doctors because not only is noncompliance limited, the Medicobox™ can help doctors decide on the next course of action, such as prescribing another drug.

In 2014, the United States healthcare rose to three trillion dollars, with a projected increase of 5.8% by 2025. The cost per capita of the healthcare system has risen by approximately 3,000 dollars since 2004, and is expected to rise by 4.8% over the coming years. Contrary to intuition, however, the healthcare of the United States strays behind other first-world countries such as Australia, France, Canada, etc. although it spends the most out of these countries.

Similar rankings; as represented in Table 1, have shown how healthcare drags behind in 2010, 2007, 2006 and 2004, along with last-place ranks in efficiency, equity, and cost-related problems in all four years:

These rankings are due to a significant amount of waste, which arises from multiple sources, the first of which is the failure of proper care delivery, in which execution of proper care processes, or methods are not able to be delivered properly to the patient. By implementing solutions towards this problem can alone potentially save approximately 100 billion dollars. Secondly is overtreatment, in which unnecessary and excessive amounts of medication and/or other treatments are administered to the patient. This not only wastes money, but also does not enhance or improve the patient's health regimen. This portion can potentially save approximately 158 billion dollars. Finally, fraud and abuse, which involves scams, and corrupt medical practices. Solving such problems would save approximately 82 billion dollars. In total, approximately 750 billion dollars are wasted by the United States, which could be used more effectively in other fields of the government. Table 2 represents this healthcare expenditures divided into its respective causes.

To create an effective analogy to provide a realization of this cost, the United States spent 757 billion dollars within the span of eight years in the Iraq war. In contrast, 750 billion dollars are simply wasted every year by the health system.

In addition, investment is not contributed to either research or development, resulting in the significant waste today. To take the example of GOOGLE®, one can first analyze the holistic revenue of the company itself—approximately 74.54 billion dollars per year. Out of this, approximately 8 billion is spent on research and development. The research and development portion of the 3 trillion healthcare budget is simply 1 billion dollars, too meager for any major problem to be resolved.

However, the most wasteful but overviewed practice today is noncompliance. Occupying a third of healthcare waste of resources, noncompliance is the origin and root of healthcare waste in the United States. As shown in Table 3, approximately 290 billion dollars were wasted in this sector in 2012, with a continual rise since.

Defined as the degree of impassiveness of a patient in adhering to advice given by a prescriber or doctor, medical noncompliance has surpassed all other crises faced in healthcare today. Medical noncompliance is a very broad issue; therefore, the term medication noncompliance, which is specifically the act of not taking medication as advised by the healthcare provider or simply not taking medication at all is used. Note that both terms medical noncompliance and medication noncompliance will be used interchangeably for the sake of a lack of confusion.

Approximately 25-50% of Americans were noncompliant with their medication as of 2012, and this value increased as the population of adults having at least one prescription increased from 38% between 1988-1994 to 49% between 2007-2010—due to the fact that more adults are administering medication. Because the number of patients with chronic diseases have also increased on average by at least 77% in older adults, one can predict a rise of noncompliance in the near future of healthcare—which would also create an expense of over at least 10 billion dollars. Over the rest of this paper, problems and solutions to the problem of medical noncompliance will be discussed, and how implementation of different solutions such as the Medicobox™ pill compliance device will increase the efficiency and cost-effectiveness of healthcare.

There is a major difference when one considers the terms compliance and adherence in terms of medical definitions. In the rest of this essay, although the terms adherence and compliance will be used interchangeably, clear distinction in connotations must be established. "Compliance", unlike "adherence", tends not to be as prevalent in the health industry as much as the word "adherence" does because "compliance" implies an obligation of the patient towards the doctor's advice over the true reality, in which a therapeutic alliance is formed between the doctor and patient, as demonstrated by the term adherence. These terms, however distinctive, will be used interchangeably throughout the paper.

To solve the immense problem of non-adherence, one must look into the current methods of adherence measurement. Adherence is measured as the percentage of the amount of medication the patient has taken over a select period of time. This generality can be specified by including the time and dosage of the administration of medication based on the prescription of the patient specifically. Other methods of measuring adherence is by determining the medication possession ratio(MPR), or determining the proportion of days covered(PDC). MPR is measured by the amount days a certain refill is supposed to persist, over the amount of days the medication is in the possession of the patient(such as the time between the first day and the day the patient comes for a refill).

This is shown below in Table 4.

The second method, PDC, is calculated by the amount of days supplied by the pharmacist over the number of days in the interval(Table 5). When both calculations lead to a percentage higher than 80%, the patient is said to be adherent or compliant.

However, both methods have subtle differences between one another. For example, for patients with 3 regimens to be administered in a day, but administers only one regimen per day would be accounted for in MPR calculations; however, under PDC calculations, the specific patient will not be accounted for until all three pills are taken by the patient. Therefore, PDC is a more accurate measure to track compliance. Both methods, along with questionnaires are used by clinics and doctors to determine adherence for indirect purposes. To measure adherence directly, direct observation of patient is done. In addition, testing of urine or other bodily fluids can be done to determine whether certain medication has been taken. However, this is rarely used as it is very costly, and inefficient for medical personnel.

Already one can view flaws in the method used to measure adherence in healthcare. However indirect measures taken by doctors and nurses are used in the twenty-first century, not only are they accurate, it is not a viable resource for the healthcare industry to use as there are multiple leeways that can be utilized by patients to provide incorrect, falsified, or misleading evidence of adherence. For example, a patient may simply bring back an empty container claiming that he/she has taken the medication; meanwhile, the remaining pills are compiled into another container, to which the pharmacist does not have the knowledge of.

This situation can simply be represented in the following case study: A 53 year-old man was diagnosed with insulin resistance and type 2 diabetes mellitus. To treat this, the doctor advised him to "modify his diet, increase his level of activity as much as possible, and finally was prescribed oral metformin to be taken with meals". However, after a three month follow-up, the patient's status does not change: his weight is the same, hemoglobin levels do not decrease significantly. The patient admits to not having enough exercise, nor did he try to change his eating habits. However, he asserted that he has been taking his medication as directed. Before prescribing another medication for the patient, the doctor first decides to check whether the patient is actually adhering to the prescription. He instructs the patient to bring in his pill bottle in the next follow-up. Next, the doctor calls the local pharmacy, and finds that the patient did come for a refill in a timely manner. In the next follow up, the patient confessed that he did not take his pills as prescribed by the doctor, his reason being that he was "too tired", or "forgot to take his medication." In addition, the patient stated that he has more pills at the medicine cabinet at his house. When using the methods of measuring compliance such as the MPR or PDC method, one can see that the current adherence measurement methods do not apply or are not helpful in this case study. Healthcare personnel such as physicians can potentially be misled when encountering such a scenario.

The problem of non-adherence has led to drastic consequences affecting the patient, the doctor, employer, pharmacist, etc. One consequence of noncompliance is the number of avoidable, unnecessary hospitalizations. A vast contribution to the cost of avoidable healthcare wastes, 213 billion dollars are wasted due to avoidable hospitalization. Avoidable hospitalization due to noncompliance not only decreases the number of patients who can be cured in a certain period of time, but it also causes unnecessary financial pressures on patients, employers and employees. Because of continual visits to the hospital and the average income being approximately 50,000 dollars in 2014, patients can no longer afford the high cost of hospitalizations. This is due to the fact that without insurance, three-day hospitalizations cost approximately 30,000 dollars—more than half of the average income of the average person in the United States. This is not including the cost of medication itself. Hepatitis C pills cost 1000 dollars per pill without insurance—meaning that a four month-period of medication can cost approximately 84,000 dollars—too high for patients to pay for them. Since more patients cannot enter the hospital for care, hospital employers can no longer receive the profits and income that they had before—as antidote, healthcare prices are increased to restore profits for the hospital. As shown in Table 6, approximately 8 million dollars can be saved by hospitals if adherence is increased, not including the great number of potential lives increased adherence can save.

Associations have also been made with increased noncompliance and hospitalization, and mortality rates. In a study of 557 patients suffering from cardiovascular disease, non adherence was associated with doubling of mortality rates and increased hospitalizations. In addition, studies have shown that higher rates of noncompliance of the patient lead to a higher risk of developing a serious disease or side-effect. Studies have also shown noncompliant patients with diseases such hypoglycemia develop and acquire other complications such as acute myocardial infarction once noncompliance has reached a certain degree. Similar results have been displayed in diabetes, in which higher rate of noncompliance can potentially lead to increased levels of glycosylated hemoglobin, blood pressure, and cholesterol levels. This leads to a higher rate of hospitalization of the patient. Statistics show that one-third of all hospitalizations involving adverse reactions are due to non-adherence. 69% of all of the money wasted in healthcare is due to this problem. Finally, non-adherent patients are 17 percent more likely to be hospitalized than adherent patients, and are subjected to a higher medical bill (by approximately 3757 dollars) than one who is adherent. These devastating statistics show us the immediate need to lower non adherence. On the other hand, increased compliance, as shown in Table 7 shows a study in which increased adherence have been linked to decreased hospitalization.

Another consequence of non-adherence is the effect that noncompliance has on clinical outcomes. Non-adherence that occurs during clinical trials are known as artifactual non-adherence. In these trials, adherence is assumed under ideal conditions—in which all medication is taken as prescribed. Such is the case of the Ideal Trial, which is a double-blind experiment where adherence is perfect:

A sample of participants are split into two groups: Group A which will receive the placebo, and Group B, which will receive the experimental drug. Neither the doctor nor the participant know which drug is administered or received. All participants take their pills as assigned and report for refills at the correct time. Data is recorded at the proper time, and a conclusion regarding the difference between the two treatments.

One can definitely infer that in reality, this does not ever happen. Statistics displays that this is most definitely false—both real world situations and experimental(simulated) situations, non-adherence thrives among the population. Non-adherence is not limited to taking medication in regards of the prescription—in clinical trials, participating in multiple trials at once is also considered artifactual due to the fact that certain drugs can conflict outcomes. This leads to misleading evidence, which interferes accurate hypothesis testing and conclusions, with results that may be detrimental to the population. Average adherence rate in trials is only 34-78%. This is in addition to the 30% who dump their medications before study visits. At the same time, deceptive and artifactual evidence can be completely unrelated to the hypothesis being tested-which leads to a waste of money, and a waste of time, as shown in Table 8.

In the following case study, low, or no adherence can cause problems in clinical trials:

A 42 year old male participating in a schizophrenia study was also participating in another study. While explicitly stating that he is not currently participating in another study, he laughed when confronted about the issue, stating "you caught me". In addition, he admitted to only take the medication when his "head felt clearer", although he had previously reported a 100% adherence by pill count.

Such a problem can occur with other individuals, which leads to a higher inaccuracy in data selection. Multiple or coupled non-adherence can lead to a higher impact on study power. For example, if approximately 30% of patients are noncompliant and do not give reliable data, then the study's results would be powered to approximately to 85% to 95%, where a true power would result to be 60% to 70%. This is further exemplified in Table 9.

Powering the data of an experiment using noncompliance is definitely detrimental. This is represented in the following case study:

In 2004, the New England Journal of Medicine published the results of a study of the Women's Health Initiative regarding Calcium and Vitamin D in relation to Osteoporosis. The trial was established to provide a supplement given over the counter to reduce the amount of fractures resulting in postmenopausal women. Such a trial involved approximately thirty thousand women, and seven years' worth of data.

Although such an experiment was deemed an achievement, results did not conclude as expected. Conclusions were made, but with multiple sources of error. By the end of the trial, an enormous number of women did not take their pills. Approximately 24% admitted to not take medication, while only 59% were taking 80% of the medication as prescribed. This was measured by a pill recount method, which actually overestimates compliance.

This creates the hypothetical question which dictates whether such trials involving so much noncompliance should be acknowledged as reliable. With an incredible amount of money put on such a project, pressures on scientists, and experimenters can be forced to make conclusions, even though such conclusions can easily be rejected. In addition, trials that may be on the path to producing drugs that may have the potential to eradicate the world of potent diseases may be biased, falsified, or simply inaccurate of the population—leading to potential damage to the entire population, or creating extraneous complications. In addition, another study involving the discontinuation of tamoxifen (trade name NOLVADEX), used to treat breast cancer, concluded that approximately 88 out of the 516 participants decided not to take medication after two years of the study. This was also accompanied with a negative belief towards the medication and a positive status towards discontinuation.

Another consequence of noncompliance is the rise of drug-resistant bacteria. Because patients do not usually take medication as directed, incorrect habits form, which threatens the patient in addition to the population. Common behaviors of taking premature, sporadic or intermittent halts in antibiotic regimens in addition to administering higher doses of medication in the beginning of the treatment regimen leads to resistant bacteria. Because of sporadic or intermittent noncompliance, drug resistant diseases develop. An example of this includes the case of tuberculosis. Because of non-adherence, patients who now contain the "secondary drug resistance" are able to occasionally transmit disease from one patient to another—which creates not only sets a panic to look for a stronger drug to kill the disease, but infects medical personnel and patients as well—creating more sick patients and therefore, increasing hospitalization. In addition, children are more vulnerable due to their compromised immunities. This is represented in the following case study: When a patient using antiretrovirals decided to take medication intermittently instead of everyday due to the fact that he could not afford the copay for the medication, he unknowingly becomes resistant to the medication. With the advent of superbugs, it is especially important to lower noncompliance rates of newly developed drugs, as if resistance of these drugs can lead to a loss of many lives, and endanger the general population as a whole.

The most important and common consequence of medical non adherence is that healthcare professionals lack knowledge or data regarding the adherence of the patient. An analogy is a wall between the patient and the doctor, whereas ideally, the doctor should be able to directly interact with the patient during the treatment regimen instead of using a somewhat qualitative approach to determine patient compliance data. Such a qualitative approach includes doctors depending on the patients to do their part, taking their medication. However, not only has it been shown that the majority of the population does not take their medication as directed, but doctors cannot receive evidence denoting the fact that the patient is taking their medication; simple word of mouth is not enough to determine whether the patient is compliant. This negatively affects doctors, who do not know why the patient is not healing.

Although noncompliance can lead to many consequences such as an effect to hospitalizations and clinical trials as well as antibiotic resistance, the reason behind noncompliance is still debated among researchers. Noncompliance comes in two different types: intentional and unintentional. Intentional noncompliance is the action of deliberately not taking medication at all or as prescribed by a health personnel. This is usually a decision made by the patient while weighing the potential benefits and harms when taking a drug. Side-effects and drug dependency may take a role in such a decision. This is due to three reasons: a lack of knowledge on the potential advantages or disadvantages when taking another medication, when the phenotypic benefits of the treatment is either not visible, or not obvious, and the physiological adaptation needed to sense the need of help or treatment. First of all, patients do not have much of a context as to how the medication will change their daily lifestyle. Clinical records simply show adverse life-threatening reactions, but never display the change in the quality of life for the patient. Because of the faulty appraisal of the medication, negative side-effects become not only an unpleasant surprise to the patient, but also taking medication becomes a burden that the patient is now unwilling to take. For example, if a doctor prescribes a new drug to a patient with a certain illness, he/she will tell the patient that the medication will "cure the illness", and help the patient in that sense, but will not tell the patient of a possible unpleasant side-effect such as getting headaches; which leads the patient to think negatively of the drug itself. Secondly, benefits of a certain drug is not visible to the patient. In the previous example, the patient may not know that his/her illness is being cured, due to a lack of phenotypic difference by the drug. Instead, the patient phenotypically experiences the side-effect, once again giving a negative envisioning of the drug itself. This is fairly common on drugs which do not have a cure guaranteed for the patient, which would lead to a questioning of the effectiveness of the drug, especially if it produces side effects without a visible benefit Table 10 displays this common, but incorrect perception.

Finally, the prospect of adapting to the fact that a patient is ill is based on the physiology of grief—in which the patient does not comply to the medication due to the fact that he or she may not want to be viewed as or view themselves as ill or sick. In addition, other unrelated issues that may cause grief may cause non-adherence. This is further exemplified in the following case study:

A 54-year old lady had a kidney transplant done when she was 24, and was in a very healthy state, and married a year after her transplant. However, after her husband passed away from a recent heart attack, she fell into a deep state of grief, which led her to temporarily stop taking medication due to her grief.

This shows how depression, although regarding a completely different issue, may affect non adherence.

However, the most important factor causing intentional non-adherence is the fact that medication is much too expensive to the average patient, and the cost of pills are increasing at a very drastic rate. For example, the costs of cancer drugs have been increased from $5000 to $10,000 before 2000, and over $100,000 in 2012. BIOGEN IDEC®'s drug for multiple sclerosis costs $54,900 per patient every year, in addition to Hepatitis C drug costs of $84,000 and Cystic Drug costs of $25

With the average income per person being approximately $51,000, such medication is definitely unaffordable by the general public. This induces medical non-adherence because it changes one's attitude towards the medication, causing him/her to behave adversely. These behaviors include taking pills every other day, taking half a pill every day, or simply taking medication when the illness is strong. Approximately 32% of older patients take less medication than prescribed to avoid high costs. This is done by either sporadically taking medications, especially when pain is received, splitting pills in half to make the prescription last longer, or delaying refills. This halts or delays the healing process, leading to ineffective and inefficient care. In addition, patients also simply discontinue the treatment. This is exemplified in which 15% do not fill out a new prescription. Out of those who do, 50% discontinue using the medication after six months, which creates major losses in the pharmaceutical industries (Table 12).

However, intentional non adherence is definitely not as drastic of a problem as unintentional non-adherence.

Unintentional non-adherence is a more significant and widespread problem in comparison to intentional adherence. Unintentional non-adherence is the result of the patient is willing to adhere to his/her prescriptions but is unable to do so due to obstacles that cannot be controlled by the patient. This includes not being able to recall whether medication has been taken, or not being able to find the medication, etc. Such a problem is very detrimental to pharmaceutical industries as well as other medical industries. In a study involving approximately 24,000 subjects, approximately 62% forgot to take their medication, 37% ran out of medication, and 23% were simply too careless. This is in comparison to only 33% who decided not to take medication intentionally. Unintentional non-adherence involves many different factors, such as age, race, gender; education, etc.

The first factor that will be discussed is age. Age plays a significant role in the elderly population because of the many challenges that they have, such as physical and mental disabilities. Studies show that approximately 40 to 75% of the elderly population do not take medication at the proper time, or the correct amount of medication required due to consequences such as a decreased cognitive and/or physical abilities that are present in higher rates in a younger adult. This is illustrated in Table 13.

In addition, elderly noncompliance accounts for approximately 26% of hospitalizations, and 25% of preventable adverse drug reactions. Finally, elderly noncompliance has caused a waste of billions of dollars in the healthcare industry. However, disputes have occurred based on whether age is a true contributor to noncompliance. For example, in a study based on fecal occult blood screening, compliance was at its peak for ages near 70, but slowly decreased at 80 years of age and 55 years of age.

A second factor that will be discussed is gender. Although there may not seem much of a difference between non adherence rates of men in comparison to women, associations do exist between gender and compliance. For example, women 27% are more likely to be non-adherent than men. Although research has not yet provided a transparent line as to why this tends to happen, explanations have been provided by researchers for this reason. These speculations include the fact that women are perhaps more price-sensitive to paying for out-of-pocket medication, or having a different level of health literacy, which is one's ability to process health information. On the other hand, studies also show that males are related to poor adherence. In one such experiment, males were 15% more non-adherent than females. Although these contrasting studies have yet to be confirmed, gender remains to be a significant factor for noncompliance. Distinctions of proper medication intake in males and females occur by as much as 10%.

A third factor that will be discussed is race. The relationship between race and noncompliance is widely studied among scientists. Caucasians are more likely to have better compliance than Blacks, Hispanics, and other minorities. Although there has not been a consensus behind why this occurs, a plausible explanation may be due to socio-economic barriers and language barriers in these minorities.

Multiple solutions will take place in response to problems stated above. The first solution to the immense problem of medical non-adherence is education. By having the knowledge and understanding the logical reasoning behind taking medication, patients can start increasing their personal rate of adherence. By utilizing education, intentional non-adherence is now decreased due to the fact that the patient will understand that although the cure will not be phenotypic, the medication is benefitting the body. In addition, by educating the public, new financial priorities may be set by the patient after considering the now-learned consequences and dangers of non-compliance. By prioritizing one's finance, the patient is able to pay off medication bills. Behaviors such as taking half a pill, or simply disregarding prescriptions may be nonexistent. Speculations behind the actual benefit of educating the non-adherent populations have been confirmed with numerous studies. For example, in a specific study, diabetes self-education program was tested to examine whether testing would lead to higher adherence rates. The results showed that approximately $415 can be saved by each patient who completes the education program (approximately 12 hours), over the span of three years. Over ten years, it is estimated that there would be a 12% decrease in coronary heart disease events, in addition to a 15% decrease in microvascular disease events.

Education also helps diminish the problem of health illiteracy—a significant problem in healthcare today. Defined as the ability for a patient to obtain, access, and understand health information and services to make appropriate health choices, health literacy has become a significant problem for patients and healthcare providers over the recent years. Approximately only 12% of adults have proficient health literacy. In addition, only 33.3% are able to do menial tasks properly, such as following directions on the prescription. Health illiteracy then becomes a concern because of the fact that the patient may not be able to determine when he/she has to take their medication. In addition, poison warnings or other hazards will not be read or understood, leading to hospitalization or a more extreme event—death. This also leads to shame of a patient, in which the patient is too embarrassed or ashamed to ask for help. In a study, approximately 85% of those who were illiterate did not admit it to their coworkers, and 50% hid their illiteracy from their children. An important factor in health literacy is numeracy. Being the ability for one to understand numbers, this factor is crucial to understanding health information. However, in this field itself, numerous patients struggle to comprehend simple numerical data. Studies show that 16% of highly educated individuals were unable to determine which has a higher risk: 1%, 5%, or 10%.

Education is also associated with the perception in which the patient is in control. In this case, by letting the patient receive the power to make his or her own choices, he/she is then actively participating in the pathway for successful drug compliance. Examples such as allowing the patient to decide when to take medication over having the doctor of pharmacist make decisions for them. Therefore, if the patient prefers taking medication in the morning over the evening, there is a higher probability of adherence in the morning rather than if the pharmacist forces the patient to take medication at night. In addition, medical personnel can also determine the motivation of the patient to cure their ailments, and determine adherence predictions before the patient takes medication. In conclusion, the multifactorial solution of education is able to limit the outbreak of intentional noncompliance in addition to unintentional noncompliance.

The second solution is to promote effective communication between the doctor and the patient. Studies show that poor communication with one's healthcare provider is linked to patient noncompliance. In addition, a study showed that compliance of the patient increased when the doctors are emotionally supportive, and provide empathy towards the patient. It is important for this to happen, as miscommunication can reduce transparency between the doctor and the patient, which usually occurs with multiple medication prescribers. It is shown that patients with multiple physicians and healthcare providers prescribing multiple medications tend to lose confidence in their health regimen. To solve such a problem, patient empowerment is needed. By allowing the patient to actively participate in the health regimen, doctor and patient communication occurs without hesitation by the patient. In addition to empowerment, it is important for patients to share all fallacies in their regimen to their physicians. For example, it is common for patients to admit to noncompliance when prompted, as exemplified in the case study. As displayed on Table 14, this also creates an ill-transparent disparity between the patient and the doctor. As shown in the Table 14 below, patients do not reach the ideal medical practices region, creating a gap between the patient and the doctor.

The third solution is to create an effective reminder system, one that is able to remind the patient to take their medication in addition to maintain compliance of the patient. As established above, unintentional noncompliance is most prevalent due to the fact that patients tend to forget to take their medication. Commonly found in the elderly sector, it is imperative to solve the overarching problem of carelessness and forgetfulness of patients. Reminder systems are effective because they allow the patient to not only take the medication that is required for their health regimen, but also allow the patient to get habituated in taking medication regularly. These reminder systems are only effective, however, if patient contact is at its highest. Therefore, it is important to understand the patient, and accustom the reminder system to how the patient communicates with his/her environment.

To be able to increase communication and prevent unintentional compliance, it is suggested that effective use of technology will be the most cost-effective and efficient to improve the healthcare system. With the coming of the twenty-first century, multiple devices and gadgets can be used in the healthcare system to reduce medical noncompliance. Technology is a very viable instrument that the system can use as it is very inexpensive, but is also very effective in enabling adherence. With the coming of new robots and wireless devices, the idea of using technology is more appealing than ever. However, the technology being implemented in the medical industry today is outdated, and has many flaws, making it less applicable in the 21st century.

One such technology utilized by pharmacists is the use of databases to allow for automated reminders to take medication though automated text messages, emails, and calls. Information regarding the date and time of automated messages would be received by computing metrics based on MPR data—involving the amount of days the patient had access to his or her medication. However, such technology is very inefficient and not beneficial. In a study involving 398 patients, using automated reminders along with monitoring devices did not show any significant benefit to medical adherence. Another study has also showed similar results—in a study with 275 patients, no significant benefit occurred with interventions such as automated and personal phone calls. Such use of technology is not very successful in healthcare today because of multiple factors. First, any benefits in adherence is only intended towards the patient, whereas doctors will not know the health regimen for the patient in terms of adherence. At the same time, pharmacists do not know for sure how many pills the patient took in a select time period. Because of this, neither doctor nor the pharmacists know whether the patient took the medication or not. This leads to the second flaw: the method is not flawless. Instead, it is far from determining actual adherence. Patients can simply decide not to take medication without notifying the doctor or the pharmacist, in addition to ignoring or subscribing to stop automated reminders. When these two effortless procedures are taken, the database is simply useless. Finally, automated reminders are simply not effective in reminding patients to take medication. Reminders can be simply ignored by the patient, and also, the patient can simply turn off reminders from pharmacists (As daily automated reminders can be irritating to some). Therefore, databased and automated reminders and adherence predictions are not effective due to its impracticalities.

Another form of technology involves writing prescriptions, called e-prescriptions, in which prescriptions are written electronically rather than by hand. This makes a major difference because handwritten notes are easily misplaced by patients. In addition, handwritten notes do not provide any verification that the patient came to pick up his or her medication. This behavior usually goes unseen because pharmacists are not aware of the fact that the doctor has prescribed medication to a specific patient. By using electronic prescriptions, pharmacists are able to verify and determine whether certain medication is supposed to be picked up by the specific patient. Also, refills of medication under the awareness of the pharmacist can counter patient forgetfulness to take medication again. Unlike automated phone calls by database-related pharmacies, e-prescribing has led to a benefit in terms of the amount of prescriptions filled (as shown in Table 15).

However, it does not solve the entire problem. There are still many aspects of noncompliance not covered by the idea of c-prescribing. First of all, although there is an increase of prescription pickups, e-prescriptions do not affect the aspect of patients taking medication at home. Secondly, errors occur between pharmacist and doctor communication (due to software problems) which would lead to decreased efficiency. Approximately 1 out of every 10 prescriptions sent result in pharmacist intervention because of a lack of specificity or other complications. More importantly, however, is the cost of such technology. Per prescriber, the cost is approximately 2,500 dollars, too expensive for the average physician. Although electronic prescriptions are helpful to some degree in decreasing noncompliance, its expenses are simply too high for a practical solution.

Although one can see the flaws in the multiple outdated technologies above, the idea of using technology is not diminished. Instead, new technology is implemented to create the items found in a patient's daily life "smart", meaning that they have enhanced features to accommodate for noncompliance. The most effective of these is the pill-bottle, which is simply the remodeling of the standard pill bottle found in pharmacies into one that is able to do much more than serve simply as a container—a "smart" pill bottle. They are especially beneficial because of the fact that a patient(ideally) is in contact with a medication bottle frequently. Due to this fact, it is easier, and more effective to create the "smart" component in a pill bottle over other medication interactions. An example would be creating a pill bottle that can also remind patients in addition to holding medication.

When discussing pill bottles, we must acknowledge the important factors needed in a pill bottle. By looking at the analysis above, it is determined that the following factors/problems/solutions must be addressed in a pill bottle: communication between doctors and patients, reminder systems in the elderly population, cost-effectiveness in the device, decreased inefficiency of the patient and the doctor, and flawlessness. Before discussing how the Medicobox™ pill compliance device successfully achieves these factors, it is important to see how other pill bottles are designed, and the flaws in their device.

The first device that will be discussed is one that uses a weight sensor to determine compliance (WO 2013127564 A1 of Femtotools AG). In the case of a weight sensor, multiple instantaneous calculations are done to determine compliance. First, the weight of each pill/medication is taken separately. Next, the weight of the entire container is measured. Every time the patient takes the medication, the device will recalculate the mass. The now decreased mass will indicate that the pill has been taken. Although such a scenario is ideal, it is not as practical as envisioned. Any roughness in the environment can now ruin the weight sensor accuracy. In addition, in the case of placing the pill bottle on its side, the reading of the weight will not be accurate at the slightest, and also damage the weight sensor. Finally, the device is relatively in a higher amount of weight, creating an impracticality in the field of portable devices.

Another popular device in the market is the MEDSMART PLUS®Monitored Automatic Medication Pill Dispenser (UPC 837066001289), a device that can send a text message, call, or email to the caregiver if the patient does not take his/her pills within one hour time. This will occur along with sounds and blinking lights to indicate that the patient has not taken pills. This blinking light can be stopped only when the patient actually takes the pills. Unlike the bottle before, this device is able to be transported easily, and can run on batteries. Although such features seem beneficial, it does not fit the criteria established. The dispenser is incredibly expensive, as it costs at least 800 dollars. In the average population, patients are not able to afford such a device. In addition, although the patient's compliance is sent to the doctor, it cannot be organized in a way so it is easier for the doctor to be able to access them. In other words, long term compliance tracking is not achieved by the device in discussion.

Yet another pill case called the MEDSIGNALS pill case. Unlike the other pill bottles, this is able to all the same functions, along with being able to connect to one's landline, and contains a speaker which can speak out instructions to the patient regarding how to take the medication. Similar to other devices before, the device can produce lights and beeping sounds to alert the patient to take the medication. For all of these features, there must be a power source to charge the device.

Another prior art device is disclosed in US 20160324726 A1 of Roberts et al for a Smart Cap For a Medication Container. Robert's '726 uses a weight sensor to detect reduced overall pill capacity weight by virtue of one or more pills being retrieved by the user. Roberts '726 makes use of a bluetooth chip (BLE) connected to a smartphone app. Roberts '726 also uses an RFID Tag which can store information and can release it when a computer is in proximity, and a signal amplifier to amplify the bluetooth and weight sensor signals.

As seen in these top-market pill bottles, the devices are not efficient or cost effective. Nowhere in the market can one see a device that is beneficial also to the doctors and the pharmacists in conjunction to an effective communication between the doctors and the patients. In addition, most of the devices that are available in the market tend to be too expensive for the common patient.

OBJECTS OF THE INVENTION

The inventive pill compliance bottle or container, referred to as a MEDICOBOX™ pill compliance bottle or container, is able overcome the shortcomings of the known art, including solving one or more problems in medical noncompliance at a very low price.

In contrast to aforementioned prior art pill compliance and dispensing devices, the present invention, known by the trade name "MEDICOBOX™", is a pill compliance bottle or container that functions to satisfy important problems in medical noncompliance at a very low price.

It is also an object of the present invention to provide a pill compliance device which can detect adherence and non-adherence of a medical patient's pharmaceutical treatment regimen, which utilizes detectable signals which can be transmitted via a Smartphone or via a Wi-Fi connection to the Internet to the Cloud storage media, without a separate dedicated signal transmitter and which promotes patient adherence to his or her treatment regimen.

Other objects will become apparent from the following description of the present invention.

SUMMARY OF THE INVENTION

The MEDICOBOX™ pill compliance bottle or container is a pill bottle container that is able to fit the criteria established above. The phrases "pill compliance bottle, "pill compliance container," "pill compliance box," "pill bottle," "pill device," "pill container," "pill compliance device" and "device" (such as MEDICOBOX™ device) are used interchangeably herein to describe the inventive device. The pill compliance bottle or container is able to accomplish this by the utilization of two major components: the device itself, and a smartphone app. The MEDICOBOX™ pill compliance bottle or container involves three parties—the patient who will simply use the device similar to that of any other pill bottle, the doctor, who will be able to see the compliance information on an applicable To briefly summarize the process, first, the inventive pill compliance device is activated with the pushing of a button. By pushing a button, the patient is able to take his/her pills. In addition, the "smart" feature of the device is also activated. By pushing the button, a Bluetooth® signal is sent from the device to a companion smartphone app. The app itself will receive the signal, and calculate the date, time, medication, and other necessary information. With this data, the app connects with a GOGGLE® sheets document in the patient's GMAIL® account, and adds the information to the next row. The GOOGLE® sheets can then be shared with pharmacists, doctors, and other medical personnel. By using a GOOGLE® sheets account, the healthcare providers are able to create charts, data tables, etc. to accommodate to their needs.

In an alternate embodiment shown in FIG. 18, a neodymium or equivalent magnet activates the switch. For example, a reed switch can be used, which is activated when the switch is in proximity to a neodymium magnet. It is associated with a magnetic sensing circuit.

This application first discusses the inventive pill compliance device itself. That is, the MEDICOBOX™ pill compliance device will be discussed into two separate parts: Physical components and Software components. The physical components will first be discussed.

In the alternate embodiment, the inventive pill compliance box or device holds designated amounts of pills, and generally comprises a cube with a top portion having a wider width than the main pill storage compartment, so that the top portion is cantilevered outward beyond the foot print of the lower pill storage compartment. The top lid portion is wider to be able to fit over the narrower storage container. Other possible shapes, such as a cylinder, can be used, instead of a four-walled box container as shown. The top lid portion, when viewed from above, has a pair of opposite located beveled indentations, for griping the lid, for removing it off of the main ill storage box below, as well as providing areas for fasteners, such as screw, for tightening the upper lid portion upon the pill storage portion, if access needs to be controlled when the pill compliance device is not in use. The aforementioned neodymium or equivalent magnet is located in the top lid portion, so that, upon the removal of the lid from the pill container box, the magnet is now out of range from the reed switch, which is located in the bottom electronics storage base portion of the pill compliance box, which has a hollow region, including a raised platform support bracket (i.e. "stage" area) to hold the microcontroller module, which is preferably a particle IoT device, such as an esp8266 Node MCU, to facilitate wireless communications, which is faced downward so that indicator lights are visible from the bottom floor of the housing of the pill compliance box, through a plurality of holes, such as, for example, three holes. The indicator lights are preferably three lights, one each hole, for disclosing whether the device is running, what code is used and if there are any malfunctions of the device. A usb compatible port hole is provided at a lower portion of one of the upright exterior walls of the pill storage comportment, in the vicinity of the hollow bottom base staging area for the electronic components. The port hole connects to a micro-usb located on the IoT chip, for ease of uploading code onto the IoT chip. The bottom hollow base floor area portion preferably has a plurality of fasteners, such as hinges or equivalents, to prevent components from falling out of the device. The bottom base floor portion is a separate hollow region of the pill container box which stores a power source, such as, for example, an 1800 MaH LIPO battery, or an equivalent power source battery, which is connected to the pcb (PC board). A manually operable push button is used to facilitate opening the pill storage compartment, and for electronically notifying care givers that the patient has obtained a daily dose pill or other orally ingestible supplement. The push button is connected to the IoT device.

Structurally, in the alternate embodiment with the removable lid having a magnet therein, the box is beveled at opposite sides, to facilitate manually pry open the device. The container also has a port on the side of the box, for insertion of a micro-USB into the IoT device for programming.

The main physical component in the inventive pill compliance device is a microcontroller on a circuit board that contains multiple electronic components, in addition to the microcontroller, such as memory, voltage regulators, switches, sensors, pick-up devices, and a Bluetooth module, etc., as known to the skilled person. The microcontroller includes a programmable processor or CPU along with memory and programmable input/output devices. In the alternative, the main physical component is a system on a chip (SoC), which includes a microcontroller as one of its components. The present invention uses the circuit board and components, or SoC to process any code or instructions programmed into and/or received by the entering the MEDI-COBOX™ device, and to process signals from the push button or from the reed switch in the alternative embodiment, to send one or more signals to the Bluetooth module or Wi-Fi module (which will be discussed herein later), that are in communication with the MEDICOBOX™ device.

The microcontroller, whether on a circuit board of SoC may be programmed by accepting code via a USB port. In other words, the microcontroller or MEDICOBOX™ device is able to be programmed by a computer or computer server through a simple USB connection. To facilitate the USB connection, a USB compatible port can be provided a wall of the portion of the device having the electronic components therein, such as, for example, within a lower staging area underneath the pill storage compartment of the device. This is important because of the fact that it does not need additional circuits to program the device. Any errors in the device can simply be fixed by a re-insertion of the code itself. Finally, the microcontroller, whether on a circuit board of SoC has a power input at (preferably soldered into) the circuit board, that also may operate to charge a battery. Preferably, the battery is easily replaceable and battery types can easily found in stores. Both features are especially important for both the patient and the pharmacist because of the fact that troubleshooting is very simple to accomplish—it simply takes one to reset the code with a USB cable to restart the device once again. At the same time, patients have the option to have rechargeable batteries, which simply need to charge for a short time before proper functionality returns. One example of a power source battery is an 1800 MaH LIPO battery, or an equivalent power source battery, which is connected to the pcb (PC board).

The second most important component of the inventive pill compliance device is the Bluetooth® module. Such a module is important in communicating with the smartphone app from the device. In one embodiment, communication from the MEDICOBOX™ device is carried out using Bluetooth®, a standard for transmitting and receiving signals within short distances (10 meters). In this first embodiment, Bluetooth® is preferred over other signaling types such as radio, Wi-Fi, etc., because Bluetooth is able to ease communication between the ANDROID® app and microcontroller, whether on a circuit board of SoC. Secondly, unlike Wi-Fi, Bluetooth can be used in areas where Wi-Fi is not available, and is convenient when travelling. Finally, Bluetooth is a very inexpensive form of communication—as the Bluetooth module costs approximately one dollar. The Bluetooth® module itself is preferably a low-power transmitter, in which battery power is not used significantly—this allows the battery to last for a significant amount of time.

However, in a second embodiment, a reliable Wi-Fi module can be used for communication between the device and Smartphone. The Wi-Fi module preferably is a Particle Photon IoT unit Wi-Fi module or router. In a second embodiment, the Wi-Fi module or router receives a signal from the device and sends the received signal through a user computer electronically connected to the Wi-Fi module or router (for example, via the user's browser) via the Internet either directly to a Cloud storage media, or to a server that reroutes the received signal to the Cloud storage media. The user signals are privately stored in the Cloud storage media where they may be retrieved by authorized personnel, such as a patient's treating physician, also over the Internet. While not being limited, in one example, the IoT microcontroller may be an esp8266 Node MCU.

In an alternate embodiment, which includes the aforementioned reed switch, a tall rectangular or cylindrical container is used to house the medication. This container has a removable lid with a magnet attached that operates and interacts with a reed switch strategically mounted in the medication compartment such that every opening and closing of the container is detected (and interpreted) by the inventive pill compliance device as the patient accesses (and uses) the pills pill or tablets found in the container. The electronics that are responsive to the signals generated by the reed switch are in a sealed port of the device, such as a separate compartment, located at the bottom of the medication compartment.

In yet another embodiment, the inventive pill compliance device is in the form of a pill bottle with the driving electronic (such as a switch, electronic control and communications components) housed completely in the bottle cap. In this embodiment, Bluetooth® communication and a cell phone are not needed since the microprocessor module selected has wi-fi capability and directly communicates to cloud storage in this manner. Either a rechargeable cell such as a Lithium polymer (LiPo) cell or a replaceable primary cell maybe configured to power the electronics (also maintained in the cap). The intended operation (i.e., pill access) is detected recorded by the inventive pill compliance bottle once the bottle cap is removed and then returned to the bottle. Although a mechanical switch can be used to detect screwing off and then screwing on the cap, a switch printed circuit board (pcb) with a capacitive touch sensor and a floating ring and a press pad is preferred.

Unlike the prior art of Roberts '726, the switch and electronic communications components are housed in the pill container cap, and activated by a twist-off movement of the cap. Once a twist off of, the cap is detected, the inventive device alerts the person (in the future) through email or iPhone messages rather than contemporaneous sound/visual alerts from the device. The sensor that detects the twisting on and off of the cap preferably embodies a press plate (or the contacts in a Reed switch), which conducts a charge when pressed upon. The charge would then power the device. The charge serves as a detectable event. The power is supplied by the battery/super-capacitor.

The press plate senses the opening and closing of the bottle cap from the bottle, and a super capacitor is deployed to harness energy from a battery cell and supply it to the microprocessor, such as, for example, an esp8266 wifi board. The energy for the electronics is stored in the capacitor, and the energy comes from the battery to the capacitor, rather than just coming directly from the battery. The function of the capacitor is to be able to supply the large current needed by the esp09 microprocessor module. If the user tries to draw 70 ma of current from a battery in such a short time, the battery will die within hours. However, if the user can take this current from a capacitor (which can supply current quickly), the battery can slowly recharge the capacitor without losing its capacity.

The inventive device. device is directly connecting to wifi, obviating a need for a smartphone app receiving software receives data from the inventive pill compliance bottle (device), which can optionally be GOOGLE® databases, a web portal, or an IP address that receives patient information. That is, this embodiment of the inventive pill compliance bottle (device) utilizes a website to display data to the patient, pharmacist and physician in an intuitive way. The receiving software is able to integrate with the patient's current EHR (electronic health records), regardless of its physical or electronic location (e.g., across the country). The software stored in a memory and operational in a microprocessor or the like included in the electronics. is compatible with many current hospitals and physician's systems that rely up EHRsphysicians.

The inventive pill compliance bottle (device) is user activated. The inventive pill compliance bottle (device) implements this function in any number of ways, for example, using a "push button" switch, a slidably openable lid that detects each open or close, or a removable lid with a magnet communicating with a reed switch, where the magnets movement relative the Reed switch activates, or a cap having all electronic components therein, a removal of which is detected to cause activation of the wireless signaling components (by a switch located near the other electronic components).). The push button is a device component that is able to generate a digital signal when pushed. The signal is preferably stored either in a buffer or in some other type of memory storage element. In a preferred embodiment, the push button will send approximately one byte every time to the microcontroller is pressed (actuated). Although it is very simplistic, it is key to determining whether the patient has taken the medication or not. To prevent accidental button presses, the button contains a resistor factor, which will add a certain amount of resistance when it is pressed, as is the case with a trigger on a hand gun or other firearm. Because of this, accidents such as toppling the bottle will not trigger the push button. In alternate embodiments, the digital signal activating the microcontroller and wireless communication, is caused by slidable movement of the top of the pill storage container, or by removal of a lid therefrom, to move the magnet within the lid to be out of range from the reed switch, which is then activated to generate the digital signal.

At the same time, extensive technology such as infrared sensors, etc., to detect whether the patient has taken his/her medication because of the fact that extensive additions can increase the price of the device by a significant amount, and are also too large to practically insert in the device. However, future devices may have these additional features.

In an embodiment, the invention provides a pill compliance device for maintaining a patient's pill supply and monitoring the patient's access to pills contained in the device to memorialize the patient's compliance with his/her pill-taking regimen. The pill compliance device comprises a housing, including an inner pill or capsule storage compartment and an electronics unit, a removable cover covering the inner pill or capsule storage compartment of said housing, including a magnet and a magnetically activated switch to detect removal of said cover and magnet away from said housing, and to detect a replacement of said cover and magnet to said housing, wherein, separating the magnet and cover from the magnetically activated switch triggers a transition from an active state, to a dorinant state, when the magnet and switch are proximate due to the cover's presence prior to removal, and wherein attaching the cover to the housing triggers a transition from the dormant state to an active state.

A transition from the active state to the dormant state, by removing the cover from the housing generates an access signal; a transition from the dormant state to the active state, by replacing the cover to the housing generates a pill-taken signal. If the pill-taken signal is generated within a predetermined period after the pill-access signal is generated, the microcontroller generates a compliance notification signal that is communicated to a Wi-Pi module or router within or attached to said electronics unit, to memorialize the apparent compliance. The Wi-Fi module or router may direct the notification signal to an Internet address or URL of a medical service provider or cloud storage system, where the user data of the Wi-Fi notification signal is stored and accessed by authorized users. A failure to send a Wi-Fi notification signal to the medical service provider within a "failure to take" period results in an automatic communication to notify a $3^{rd}$ party that the user has failed to take a required pill or capsule.

Preferably, a key component is included for locking and unlocking said device for preventing spillage of medication and damage to said electronics unit. The electronics unit may be located in a side compartment adjacent to said inner pill or capsule storage compaitment, or in a bottom portion of said housing adjacent to said inner pill or capsule storage compartment. The magnetic switch is a Reed switch. The Reed switch may include a push button that overrides the signals generated by switching form a dormant to an active state or from an active to a dormant state. The cover may be a cover that is slidably removable and replaceable. But in the case where the cover is unscrewed to remove the cover from the housing, and screwed down to replace the cover to the housing.

The invention also provides a microcontroller-controlled method of providing pill compliance by use of a pill compliance device for maintaining a patient's pill supply and monitoring the patient's access to the pills contained in the device to memorialize the patient's compliance with his/her pill-taking regimen. The pill compliance device comprises an electronics unit with a microcontroller and electronic components such as memory, a housing with an inner pill or capsule storage compartment for storing pills, a removable cover covering the inner pill or capsule storage compartment of said housing, including a magnet, a magnetically activated switch to detect removal of said cover and magnet away from said housing, and is responsive to a replacement of said cover and magnet to said housing, wherein separating the magnet and cover from the magnetically activated switch triggers a transition from an active state, to a dormant state, when the magnet and switch are proximate due to the cover's presence prior to removal, and wherein attaching the cover to the housing triggers a transition from the dormant state to an active state.

The method includes steps of first generating an access signal upon removal of the removable cover from the housing and inner pill storage compartment, the access signal indicative of a transition from the active state to the dormant state, second generating a pill-taken signal when, within a predetermined amount of time, the removable cover is replaced on the housing and inner pill storage compartment, the pill-compliance signal indicative of the patient's having ingested the pill, and in response to a pill-taken signal, the microcontroller generating a compliance notification signal and provides said compliance notification signal to a Wi-Fi module or router within, attached to or coupled to the electronic unit to memorialize the apparent compliance. Preferably, the device is substantially rectangular, and wherein the first and second generating steps include sliding a cover away from or onto the housing, respectively. The device may be substantially cylindrical, however, and wherein the first and second generating steps include sliding unscrewing and separating the cover from the housing and screwing the cover onto the housing, respectively. For that matter, the step of the microcontroller generating a compliance notification signal includes directly sending said signal to a $3^{rd}$ party to communicate that the user has failed to take a required pill or capsule, and may further include sending said signal to a cloud storage system, where the user data of the Wi-Fi notification signal is stored and accessed by authorized users. The step of the microcontroller generating a compliance notification signal requires generating an open cover signal and a closed cover signal in a sequence within a predetermined time period; the access signal indicates the time and date that a patient user acted to obtain access to the pills in the compartment.

Finally, to create a strong structure to insert all components into the device, a 3D printed frame is needed. The frame is created in a way such that the electrical components positioned thereon, including the microcontroller, etc., are hidden from the view of the patient.

BRIEF DESCRIPTION OF DRAWINGS

The present invention can best be understood in connection with the accompanying drawings. It is noted that the invention is not limited to the precise embodiments shown in drawings, in which:

FIG. 9 is a screen shot of patient medication dose regimen compliance data of the first embodiment, seen by a medical/pharmaceutical provider.

FIG. 10 is a computer code for use of the first embodiment of the MEDICOBOX™ pill compliance device system.

FIG. 11 is a perspective view of a second embodiment of a pill compliance and monitoring box of the present invention.

FIG. 12 is an exploded perspective view thereof, showing the housing in an open pill dispensing mode, with the locking lid shown removed in the direction of the arrow shown.

FIG. 17 is a computer code for use of the preferred embodiment of the MEDICOBOX™ pill compliance device system shown in FIGS. 11-16 herein.

DETAILED DESCRIPTION OF THE INVENTION

Figure 1:
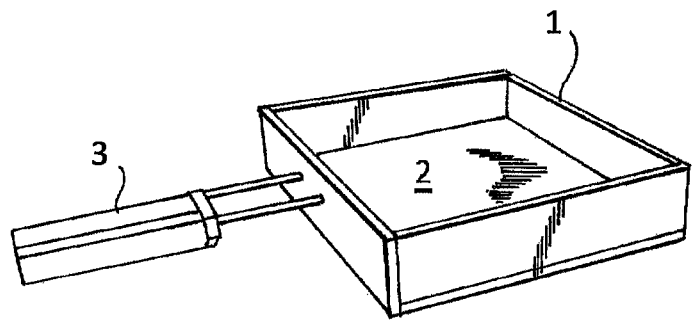
FIG. 1 is a perspective view of a first embodiment of the pill storage compartment and push button activator portion of the MEDICOBOX™ pill compliance device, shown with a cover removed.

FIG. 1 shows the inner storage compartment 2 of upper closable box container 1, in which the pills will be placed (to be administered to oneself later). The second part of FIG. 1 is the push-lever 3 which will force the pill container out of the box, thereby allowing the patient to consume the medication, including one or more pills or capsules.

Figure 2:
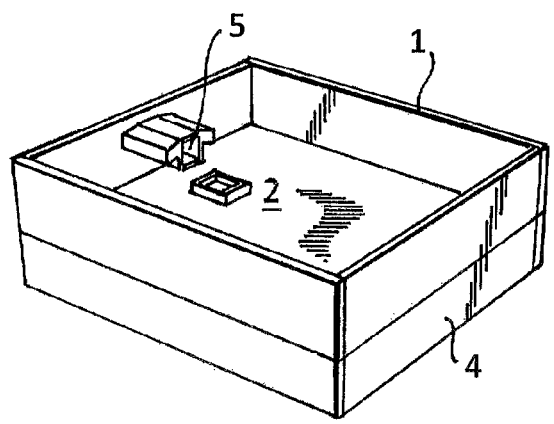
FIG. 2 is a perspective view of the first embodiment of the pill compartment and electrical components compartment of the MEDICOBOX™ pill compliance device assembled together, shown with a cover removed.

FIG. 2 provides the fundamental structure of the pill compliance device. It not only contains lower box compartment 4 containing electrical components, on a circuit board, or SoC, but also contains the upper pill storage compartment 1 of the box of FIG. 1, FIG. 2 shows the upper pill storage compartment 1 with the opening on the left, with cavity 5 for movement of push lever 3 therethrough, for exposing the upper pill container region 2 of upper compartment 1 for patient access to pills or capsules therein.

With respect to FIGS. 1 and 2, the box 2 of FIG. 1 is first placed on the upper surface of the lower support box 4 of FIG. 2. In standard position, the push lever 3 of the box of FIG. 1 will jut out of the holistic pill compliance device box.

Figure 3:
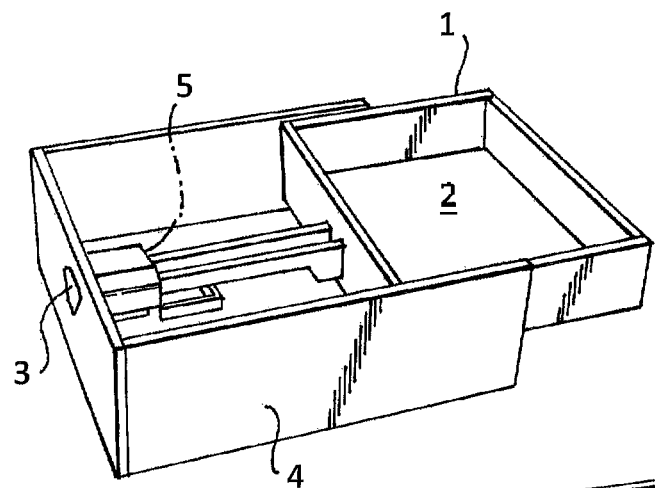
FIG. 3 is a perspective view of the first embodiment of the MEDICOBOX™ shown with the upper pill compartment slid open, above the lower electronics compartment, with the top cover removed.
Figure 4:
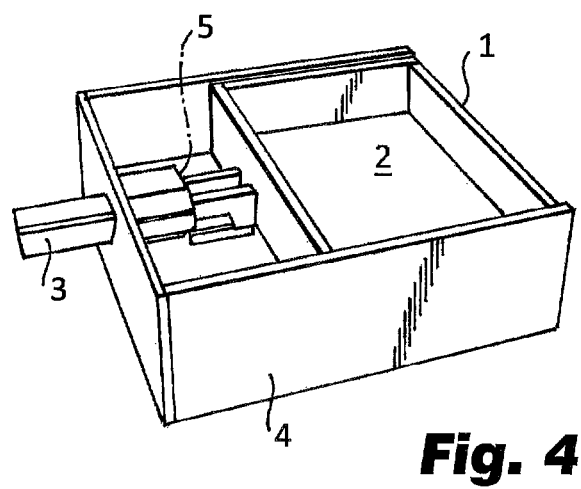
FIG. 4 is a perspective view of the first embodiment of the MEDICOBOX™ shown with the upper pill compartment in a closed position above the lower electronics compartment, with the top cover removed.

FIGS. 3 and 4 illustrate the processes of using the components shown in FIGS. 1 and 2. FIG. 3 shows the upper storage pill compartment box 1 of FIG. 1 in a "pressed" position; in this case, the push lever 3 of the box of FIG. 1 is jutting out of the general pill compliance device, which allows the patient to take the prescribed medication from medicine storage region 2 of upper compartment 1 therefrom. The push lever 3 is aligned with the exterior wall of upper pill storage compartment box 1 of FIG. 2. Such a position of the push lever 3 allows also for the pushing of an electronic push button associated with push lever 3 in the vicinity of cavity 5, which activates a switch allows for tracking the compliance of the patient. It is assumed if the patient opens the pill bottle or other supply of pills in upper compartment 1, he/she will take the medication. It is also known that in other embodiments, the pills or capsules can be emptied from their commercial bottle or other container, and stored in upper pill storage compartment 1.

Figure 5:
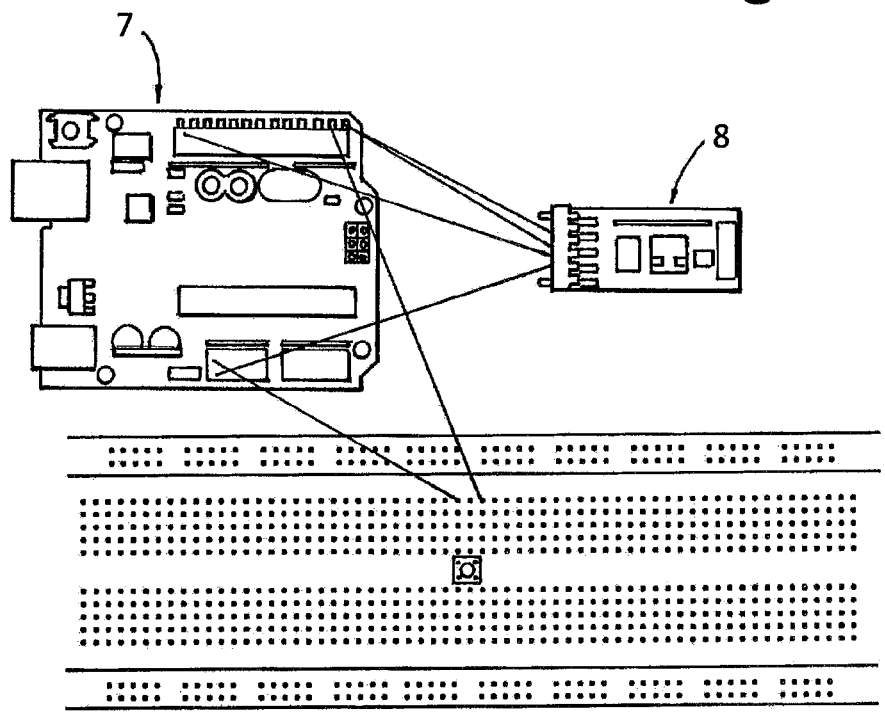
FIG. 5 is a diagrammatic photographic view marked up, showing the electronic schematic containing the various components of the first embodiment of the MEDICOBOX™ ill compliance device.

FIG. 5 displays the electronic wiring needed for the monitoring circuit to be made. To connect all components, wiring is needed. The following will exemplify one typical example, of many other typical examples, of the wiring between the three main components:

a. The electronic control device 7, such as, for example, an ARDUINO UNO®, is connected to a Bluetooth module 8, such as, for example, an HC-05 Bluetooth module at one or more connections, such as, for example, four different pins as displayed in FIG. 5, in a configuration, such as the following exemplary configuration wherein:
  i. Pin Tx (Transmitter) on the ARDUINO® electronic control device 7 connects to pin Rx (Receiver) on the HC-05 Bluetooth module 8;
  ii, Pin Rx (Receiver) on the ARDUINO® electronic control device 7 connects to pin Tx (Transmitter) on the HC-05 Bluetooth module 8;
  iii. Pin 3V (3 Volts) on the ARDUINO® electronic control device 7 connects to pin VCC (Voltage at the Common Collector) on the HC-05 Bluetooth module 8;
  iv. The Ground on the ARDUINO® electronic control device 7 connects to Ground to the HC-05 Bluetooth module 8.

b. The ARDUINO UNO® electronic control device 7 is connected to a push button switch 6 associated with at two different pins as displayed in FIG. 5:
  i. Pin 5 (5 Volts) on the ARDUINO® electronic control device 7 connects to pin A on the push button switch 6; and,
  ii. Pin 2 on the ARDUINO® electronic control device 7 connects to pin B on the push button switch 6.

Thereupon, the HC-05 Bluetooth module communicates one or more signals to a remote health care provider, such as the medication prescribing physician, which are printed in a readable format, such as in a spreadsheet 9, for example, a GOOGLE DOCS sheet of FIG. 9.

FIG. 10 is an example of the computer code used to implement the software and hardware of the electronic control device 7 and Bluetooth module 8, for communicating daily or periodic patient medication intake data displayed on spreadsheet 9 for review by the health care provider.

Figure 6:
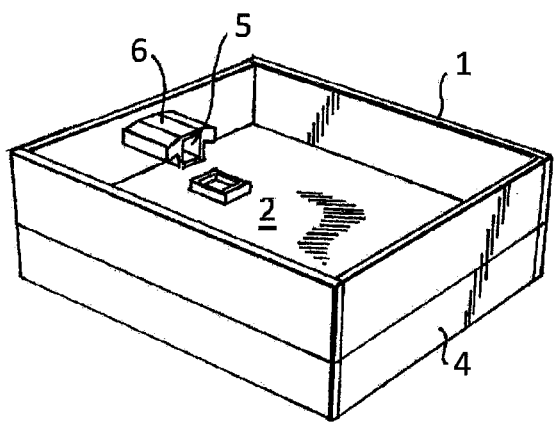
FIG. 6 is a perspective view of the first embodiment of MEDICOBOX™ pill compliance device shown without the pill container portion, and showing the mechanical interface for the activation push button mechanism.
Figure 8:
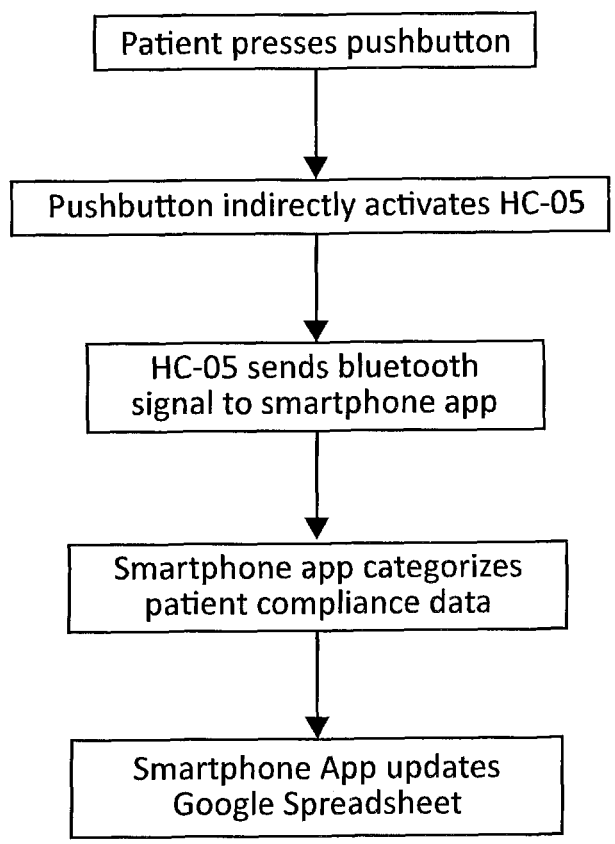
FIG. 8 is a flow chart of the software system process of the first embodiment of the MEDICOBOX™ pill compliance device.

The flow chart of FIG. 8 shows the system of the pill compliance device of the present invention, where a patient first presses the push lever 3 to activate switch 6 of FIG. 6 whereupon the switch 6 indirectly activates the Bluetooth module 8 communicating with the electronic controller device 7, whereupon the Bluetooth module 8 sends a signal to a smartphone app, whereupon further the smartphone app categorizes patient medication intake compliance data, and the computer controlled spreadsheet 9, such as a GOOGLE DOCS spreadsheet, for access by the health care provider.

This design is very beneficial because of the fact that it is childproof. Patients have the option to add a safety lock on the pill compliance device, which would avoid the spilling of medication. Also, it is very simple to use. Common bottles today, where one has to twist to receive medication, which make it very hard for elderly people to use. Therefore, this pill compliance device shown in FIGS. 1-10 simply needs one to push a button 3 to activate a switch 6 with little energy to receive their medication.

With respect to the software component in the pill compliance device, one simply has to program the microcontroller to program the entire pill compliance device because the circuit of the controller 7 is able to control and process data from the push button 3 and the Bluetooth module 8. It is written such that any changes in the state of the device is recorded as either a 0 or a 1.0 signifies that the button of push button lever 3 has not been pressed, and 1 signifies that the button has been pressed. This information is sent to the Bluetooth module 8, which automatically sends the byte through Bluetooth to its surroundings, which will be recognized by the patient and the health care provider.

The smartphone app used with this first embodiment version of FIGS. 1-10 of the present invention is automatically programmed to connect to the Bluetooth module 8 when opened. Programmed to look for the "1" from the code that the Bluetooth module 8 sends, the ANDROID® app records the time, medication, and demographics of the patient when the binary "1" is sent. After this is done, a GOOGLE® sheets page is updated to include the data from the smartphone app which indirectly gets the data from the push button of push button lever 3. This spreadsheet is then able to be shared ° with the doctor, pharmacist, etc. This is also convenient, because modifications can be made by the pharmacist or the doctor to the spreadsheet for ease of viewing. In addition, when new doctors are visited, or primary care specialists are changed, the spreadsheet is versatile enough to send itself to multiple people. Finally, because GOOGLE® Sheets is a cloud account, a very large amount of data is able to be stored without the risk of it being lost. The app specifically is able to work when the phone is in sleep mode. In other words, when the phone is on, it is able to work in the background, meaning that while the user is on another application, if the patient does take medication, the medication app will still recognize it. By being able to work in the background, and while the phone is "asleep", no mistakes are made when the patient takes the medication.

Figure 7:
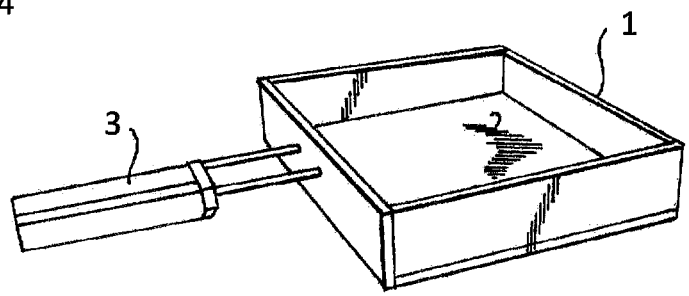
FIG. 7 is a perspective view of the first embodiment of the pill container/dispenser and activation push button portion of the MEDICOBOX™" pill compliance device.

FIG. 6 shows the MEDICOBOX™ pill compliance device without the pill container bottle, and showing the mechanical interface for the switch 6 the activation push button mechanism. FIG. 7 shows the pill container/dispenser 1 and activation push button portion 3 of the MEDICOBOX™" pill compliance device.

FIG. 8 is a flow chart of the software system process of the MEDICOBOX™ pill compliance device. For example, when a medical patient pushes the pushbutton to open the pill box to obtain a specific dose of medicine, such as one or more prescribed pills 27 or capsules, the pushbutton switch indirectly activates the HC-05 Wi-Fi module and electrical component circuitry, which then sends a Bluetooth signal to a specified Smartphone app. The Smartphone app categorizes the patient compliance data as "adherent", or "non-adherent", and then the Smartphone app updates a GOOGLE® or other spreadsheet, such as shown in FIG. 9. FIG. 9 is an example of a screen shot of patient medication dose regimen compliance data in the spreadsheet, seen by a medical/pharmaceutical provider. FIG. 10 is a computer code for use of the MEDICOBOX™ pill compliance device system. In analogous situations, instead the electronics being activated by a push button, a sliding pull button can be used, as in FIGS. 11-17, a removable cap with a magnet communicating with a reed switch can be used, as in FIG. 18, or a twist off threaded cap can be used for activating in response to the electronic signals generated when a user opens any of the inventive devices to access his/her medication therein.

The second preferred embodiment of the MEDICO-BOX™ pill compliance device is shown in FIG. 1147. The second preferred embodiment of the MEDICOBOX™ pill compliance device relies upon a Wi-Fi module 67 of FIG. 16, instead of the previous HC-05 Bluetooth module 8 of FIGS. 1-10. Wi-Fi is preferable because Bluetooth connection is prone to multiple variables, and cannot be sustained over certain distances. Secondly, Bluetooth needs an ANDROID® device, such as an ANDROID® smartphone and iOS application to serve as a go-between from Bluetooth to GOOGLE® Sheets, similar to GOOGLE spreadsheet 9 shown in FIG. 9 of the first embodiment. Thus, the Particle Photon IoT Wi-Fi Module 67 has been used in the second, preferred embodiment version of FIGS. 11-17, in place of the original ARDUINO®+Bluetooth circuit of the first embodiment version of FIGS. 1-10.

Figure 13:
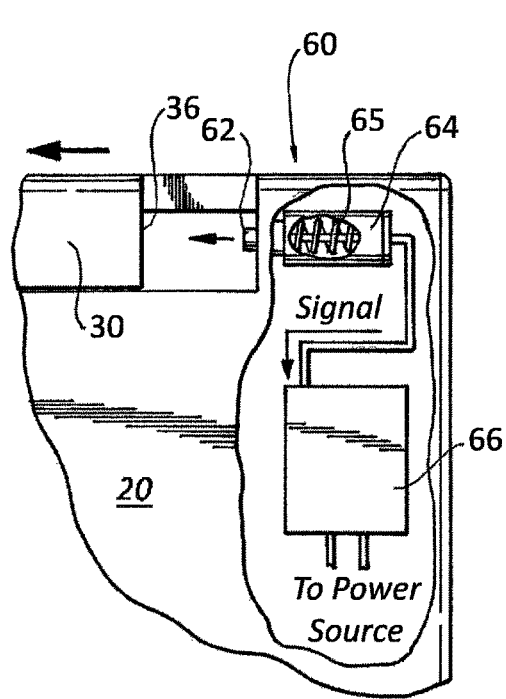
FIG. 13 is a close-up detail view in partial cutaway, showing the switch activator, switch and electronic internet enabling components of the pill compliance and monitoring box of FIGS. 11 and 12, during activation of the switch controlling the microcontroller and Wi-Fi module in preparing one or more signals to be subsequently sent to the health care provider, after a time delay, to the health care provider via an Internet storage media, such as the cloud.
Figure 16:
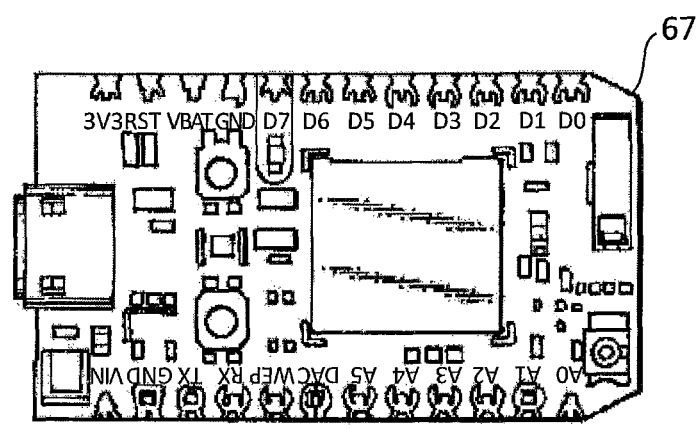
FIG. 16 is a top view of an example of a Wi-Fi module used typically with the preferred embodiment of FIGS. 11-15 herein.

For example, FIG. 16 displays the particle photon MT Wi-Fi module 67. The IoT module 67 takes advantage of Wi-Fi to send a signal through its cloud server 70 shown in FIG. 13a. The ground pin and the DO pins shown in FIG. 16 {of Wi-Fi module 67 of FIG. 13) are connected through the PC board 66, to the pushbutton switch 62 shown in FIGS. 13 and 13a; the ground pin is used to establish the connection, and DO determines what information is sent, as well as completes the circuit. As shown in FIGS. 13, 13 a and 14, the Wi-fi module 67 shown in FIG. 16 is controlled by the microcontroller in the PC board 66. The Wi-Fi module 67 and microcontroller of PC board 66, are both powered from a battery array 86 located in a lower receptacle 86 of housing 20 of pill compliance device 10, with opening 80 and cover 88 for holding batteries 86 therein, through an electrical wire associated with the circuit, displayed in FIG. 13 for the circuit. The circuit includes PC board 66, having a micro controller, to power the pill compliance device 10. Such a pill compliance device 10 receives power through the use of the array of batteries 86, such as, for example, four 1.5v batteries.

The actual process of compiling the acts of the user in opening the pill compliance device 10 is a unique two-step process with a momentary time delay.

For example, as shown in FIG. 13, first, the patient opens the housing 20 of the pill compliance device 10 by sliding the top lid cover 30 rearward, to expose the interior compartment 28 storing the pills or capsules 27 therein. First patient opens the lid cover 30, so that the leading edge wall 36 of lid cover 30 is released away from push button switch 62, which was previously being urged against leading edge wall 36 preferably by optional internal biasing spring 65 within control sub-housing 64 located in a top, preferably corner portion of housing 20, to the side of track 26 engageable with groove 32 of slidable top cover lid 30. Opening the cover lid 30 thereby causing a change in state of switch 62, so that it now is energized by its own movement, which electrically closes switch 62 to activate the power supplied to the micro controller of PC board 66. In response, the software or code in the microcontroller prepares a signal indicating that the pill compliance device 10 has been opened by the patient, and readies a signal indicating the time and date of the patient accessing the supply of pills 27 from within inner compartment 28 of housing 20 and being compliant with taking the scheduled dosage of medicine pill or capsule 27.

Figure 13A:
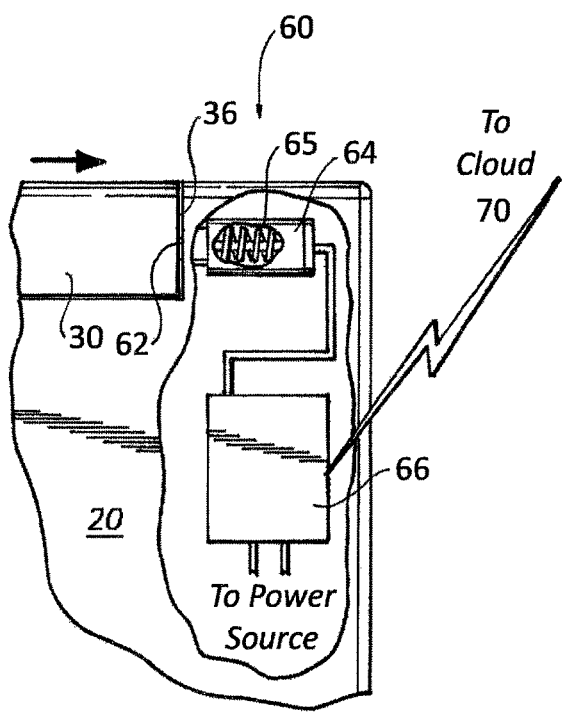
FIG. 13a is a close-up detail view in partial cutaway, showing the switch activator, switch and electronic internet enabling components of the pill compliance and monitoring box of FIGS. 11 and 12, immediately upon de-activation of the switch, where the microcontroller and Wi-Fi module send the one or more stored signals to the health care provider via an Internet storage media, such as the cloud.
Figure 14:
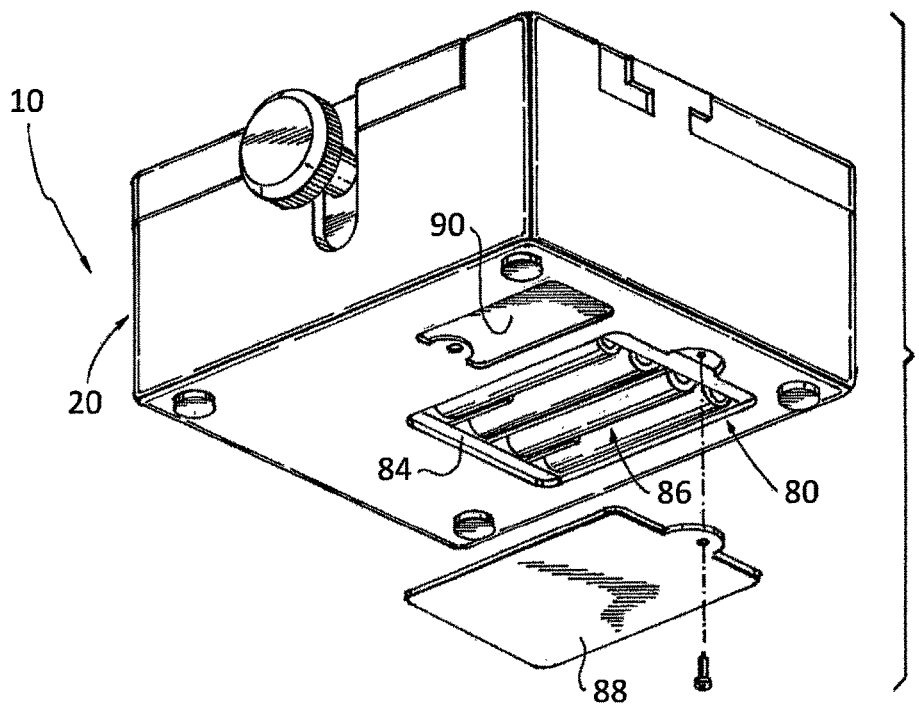
FIG. 14 is a bottom perspective view thereof, showing the power supply component of the pill compliance and monitoring box.
Figure 15:
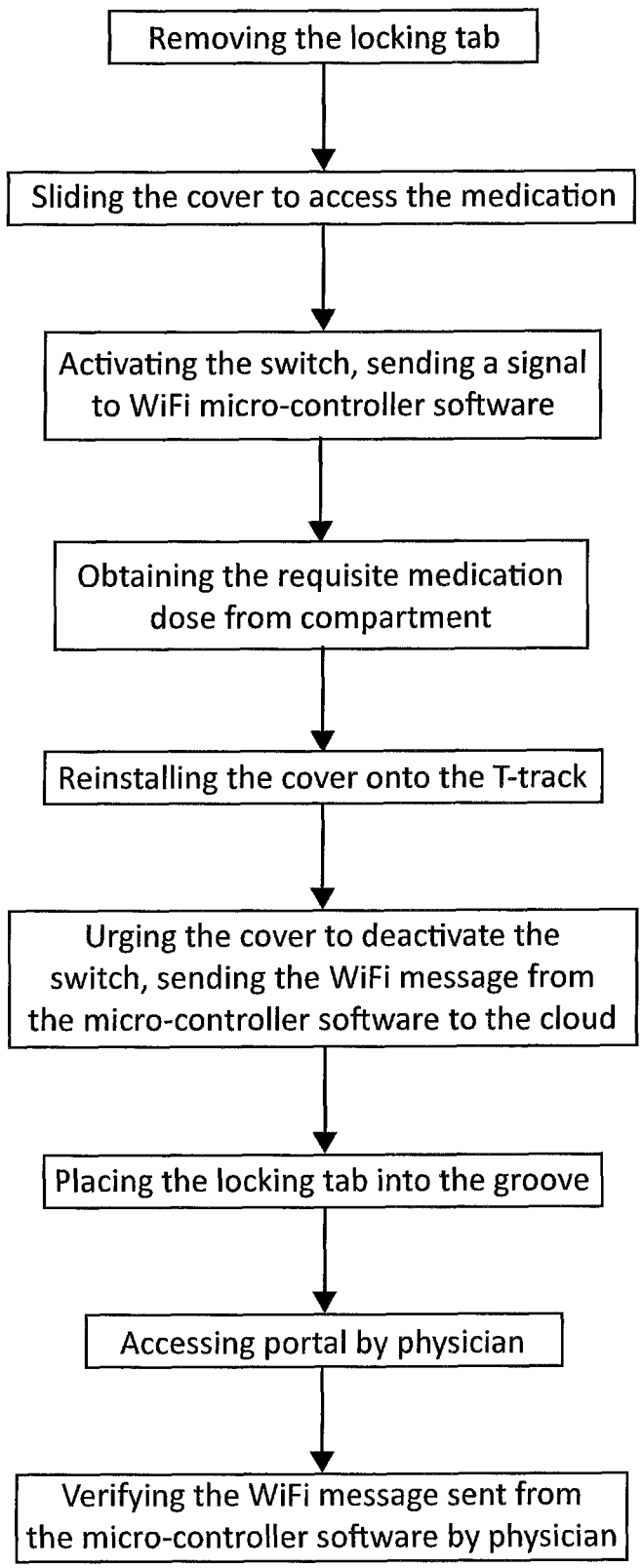
FIG. 15 is a block diagram of the medication patient activated pill compliance housing device components and associated electronic controller and internet cloud usage of the system of the preferred embodiment of the pill compliance and monitoring box.

Then, as a second step in the compliance monitoring process, as shown in FIG. 13a, the patient, having withdrawn the appropriate medication pill or capsule 27 for oral intake, then pushes the lid cover 30 back toward the push button switch 62, until the leading edge 36 of cover lid 30 re-contacts leading edge 36, thereby changing the state of the push button switch 62 from being electrically closed (capable of communicating with circuitry and electric power) into an electrically open, dormant state. At that time, as the push button 62 is de-activated when the lid cover 30 is fully closed over the open top of housing 20, the previously activated electronic software of the microcontroller of PC board 66 during a time delay preceding the dormant opening of push button switch 62, sends a delayed but activated notification signal to particle photon IoT Wi-Fi module 67. Then, as shown in FIG. 13a, when the lid 30 is fully closed, the Wi-Fi notification signal is sent to the Internet storage media, i.e., the "cloud".

In this second step of the notification process, the software associated with the microcontroller in PC board 66 and the Wi-Fi module 67 sends the Wi-Fi notification signal to the patient's health care provider or doctor in a signal capable of generating data for a spreadsheet, similar to spreadsheet 9 shown in FIG. 9 of the first, non-preferred embodiment of FIGS. 1-10, but after the aforementioned time delay during the patient's retrieval of the medication 27 from the inner compartment 28 of housing 20, because the spring loaded switch 62 is a momentary switch which is first activated when the cover lid 30 is removed. That pullback removal of the leading contact edge 36 of the cover lid 30 activates the microprocessor software in PC board 66, which prepares the Wi-Fi signal to the doctor via the Internet storage media "cloud", 70. The Wi-Fi notification signal is then sent to the cloud by the already activated time delay software when the cover lid 30 is closed shut upon re-contact of the leading edge 36 thereof with the switch 62, thereby electrically opening the switch to an open, dormant state. However, the notification signal is already being prepared by the software as the cover lid's leading edge 36 is drawn apart from the switch 62, thereby activating switch 62 and the electronic components associated therewith.

Therefore, as shown in FIG. 13 a, the second step sends the Wi-Fi notification signal to the doctor, which occurs when the state of the switch 62 is changed to "closed" i.e. activated with current flowing therethrough (the switch is "open" when no electric current is present in dormancy).

The signal to the doctor is sent by the Wi-Fi microcontroller software, because the microcontroller software prepares the message to the doctor when the switch 62 is activated by the rearward opening of the lid 30, changing the state of the switch 62 from dormant to activated.

After a time delay (the switch/button being a "momentary" switch) the software built into the microcontroller (PC board 66) is capable of sending the Wi-Fi message to the doctor when the switch is deactivated by the contact of forward wall 36 of lid 30 contacting the switch/button 62. The microcontroller doesn't need the switch to be activated; it gets ready during the "lid pulling" activation, and then when the switch goes dormant as the lid is returned to its closed position on top of housing 20, the already ready software controlled Wi-Fi knows to send its prepared message to the doctor. (The microcontroller of PC board 66 gets it power separately from the batteries 86), so even though the microcontroller software doesn't start preparing the message until the lid 30 is moved away from the switch (opening the pill compartment 28 at the same time), it separately knows when the activator switch 62 is done, and then sends the Wi-Fi message to the doctor.

FIGS. 11-15 display the physical mechanical components of the medication pill compliance device 10. The physical medication pill compliance container 10 contains three separate components put into one.

The first physical mechanical component, comprises the block 42 and key grip 44, which together are the locking "key" of the pill compliance device. This key component 42, 44 is placed inside the housing 20 of the pill compliance and monitoring device 10 to prevent the spillage of medication and damage of the electronic components. Similar to a jewelry box, this key 42, 44 must be removed from the pill compliance device 10 in order to access the medication. The key component 42, 44 fits inside housing 20 of the pill compliance device 10 simply by sliding the key component 42, 44 in a vertical plane into its compartment housing slot 34 on the top lid cover 30 and corresponding slot 24 of the housing 20 of the standing pill compliance device 10, where the slots 34 and 24 are in positional register with each other.

The second physical mechanical component is the "slider" cover lid 30 of the pill compliance device 10. The slider lid 30 has a longitudinally extending groove 32 that engages a corresponding upward track 26 on top of housing 20. For example, track 26 can have a T-shape or other joining configuration mating with groove 32 of cover lid 30. The track and groove can be optionally revised, so that the track is on the lid 30 and the groove is optionally in the top of the housing 20. The function of the cover lid 30 component is two-part. Primarily, it serves as a cover of the medication compartment 28 holding pills or capsules 27 therein. The reasoning behind such a cover lid 30 is similar to that of locking key component 42, 44, namely, to prevent spillage of the medication. Secondly, the function of the movement for sliding the cover lid off of the pill containing compartment 28 is to activate the pushbutton 62 or another type of switch, which thereby activates the electronic components including microcontroller of PC board 66 and Wi-Fi module 67. Thus, the slider lid 30 serves as a bridge between the physical components and the electrical components by activating the pushbutton switch 62, when the lid cover 30 is pulled away from the push button switch 62, so that its leading end 36 is separated from push button switch 62, urged by optional internal biasing spring 65. The actual preparation of the Wi-Fi signal from module 67 is set up during activation caused by rearward separation of the lid cover 30's leading edge 36 away from push button switch 62, but the momentary switch 62 waits until the lid is forwardly covered by the patient's manual movement thereof against the push button 62, making switch 62 dormant (again changing its logical state), but the prepared signal made during activation is sent by Wi-Fi module 67 either directly to e health care provider URL, or indirectly, first to the internet storage cloud, where it is retrieved later by a health care provider in the readable spreadsheet similar to spreadsheet 9 of FIG. 9 of the first, non-preferred embodiment of FIGS. 1-10.

The third physical mechanical component 3 is the "body" housing 20 of the pill compliance device 10 itself. While the top section lid 30 of the pill compliance device 10 is used to house the medication 27 in storage compartment 28 of housing 20, as well as to "lock" the container with key 42, 44, the bottom portion of housing 20 holds the electronic components, including, for example, the battery pack 86 as well as the microcontroller PC board 66, including, for example, an Internet connection module, such as, for example, a Particle Photon IoT (i.e. "Internet of Things" network). The Particle Photon board 67 connects an IoT network to the Internet storage media, (i.e. "the cloud"). Being the body of the pill compliance device 10, this third component (i.e. housing 20) contains the aforementioned track 26 engaging a corresponding reciprocating groove 32 of the slider lid 30 of the second component of the device 10.

As noted above, the third component (i.e. the housing 20) also has a slot for accommodating the locking/unlocking first component (i.e. locking key 42, 44) inside of it.

An enhancement to the previous prototype of FIGS. 1-10, this model pill compliance device 10 shown in FIGS. 11-17, is much sturdier and is less prone to tampering.

The use of a go-between application for ANDROID® and iOS has also been eliminated, because the IoT Wi-Fi module 67 (such as, for example, a Particle Photon IoT) is capable of pushing data through the Internet cloud, such as the patient's compliance data for opening the pill compliance device 10 for accessing and verifying daily or other periodic intake of medicine pills or capsules 27 from storage compartment 28 of pill compliance box shaped device 10, to the GOOGLE® spread sheets 9 of FIG. 9, but also for the preferred second embodiment of FIGS. 11-17, through the Wi-Fi server communicating with the Internet cloud. In general, the circuit itself has been condensed in space, and energy, as the pushbutton switch 62 and the Wi-Fi module 67, are the sole two electronic components of the pill compliance device 10, rather than three in the first embodiment version for a pill compliance device shown in FIGS. 1-10. This will therefore cut the space taken up by the device 10 by ⅓.

Figure 18:
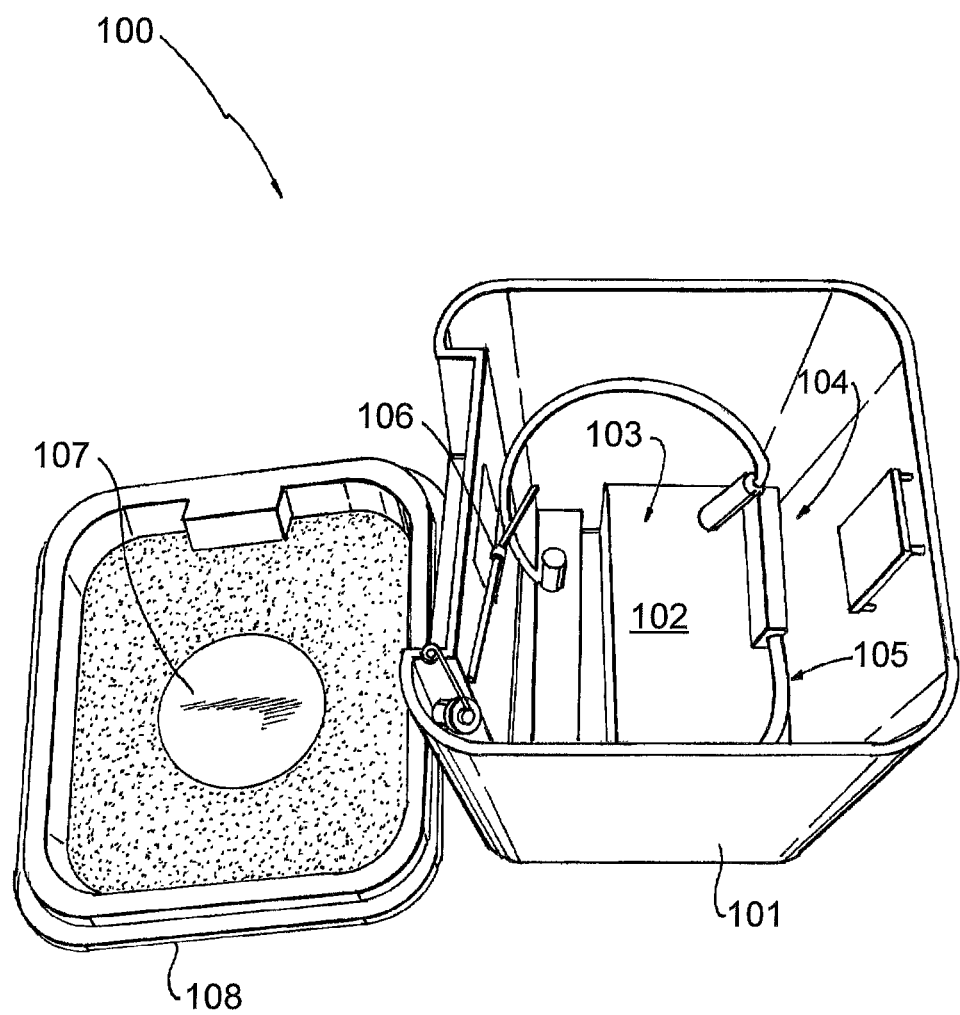
FIG. 18 is a perspective view of an alternate embodiment of the inventive pill compliance bottle (device) that utilizes a rectangular container and a magnetic reed switch.
Figure 19:
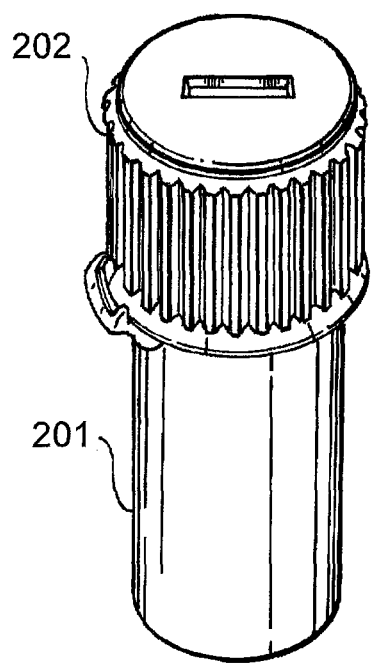
FIG. 19 is a perspective view of another inventive pill compliance dispenser (bottle or device) with a cap secured to the bottle, where the switch and all electronic components are contained within the devices' cap and activated by the twist off of the cap.[

In the embodiment shown in FIG. 18, the inventive pill compliance device 100 embodies a box-like structure that holds designated amounts of pills. Preferably, the box-like structure is a cube 101 with a top portion having a wider width than the main pill storage compartment 104. Consequently, the top portion is cantilevered outward beyond a foot print of the lower pill storage compartment 104. The top lid portion is wider to be able to fit over the narrower storage container 101. Other possible shapes, such as a cylinder, can be used, instead of a four-walled box container as shown. The top lid portion, when viewed from above, has a pair of opposite located beveled indentations (not shown), for gripping the lid 108, for removing it off of the main storage box 101 below, as well as providing areas for fasteners, such as screw, for tightening the upper lid portion upon the pill storage portion, if access needs to be controlled when the pill compliance device is not in use.

The aforementioned neodymium or equivalent magnet 107 is located in the top lid portion 108, so that, upon the removal of the lid from the pill container box 101, the magnet 107 is moved out of range from the Reed switch 106 located in the bottom electronics storage base portion 105 of the pill compliance box 101. This base portion 105 has a hollow region, including a raised platform support bracket 102 (i.e. "stage" area) to hold a microcontroller module 103, which is preferably an a IoT device, such as an esp8266 Node MCU, to facilitate wireless communications. The microcontroller module is faced downward so that optional indicator lights (not shown) are visible from the bottom floor of the housing 101 of the pill compliance box, through a plurality of holes (not shown), such as, for example, three holes. The indicator lights are preferably three lights, one each hole, for disclosing whether the device is running, what code is used and if there are any malfunctions of the device. A usb compatible port hole (not shown) may be provided at a lower portion of one of the upright exterior walls of the pill storage compartment 101, in the vicinity of the hollow bottom base staging area 105 for the electronic components. The port hole connects to a micro-usb located on the IoT chip, for ease of uploading code onto the IoT chip. The bottom hollow base floor area portion of the box container 101 preferably has a plurality of fasteners, such as hinges or equivalents, to prevent components from falling out of the device. The bottom base floor portion is a separate hollow region of the pill container box 101 which stores a power source, such as, for example, an 1800 MaH LIPO battery, or an equivalent power source battery, which is connected to the pcb (PC board) 103 in the electronics compartment 102). Structurally, in the alternate embodiment with the removable lid having a magnet therein, the box is beveled at opposite sides, to facilitate manually pry open the device. The container also optionally has a port on the side of the box, for insertion of a micro-USB into the IoT device for programming.

In FIG. 18, the microcontroller on the circuit board 103 that contains multiple electronic components, in addition to the magnet-sensitive Reed switch 106, any of a, microcontroller, memory, voltage regulators, switches, sensors, pick-up devices, and a Bluetooth® module, etc., also are included. The microcontroller includes a programmable processor or CPU along with memory and programmable input/output devices. Alternatively, the inventive pill compliance device (e.g., box) embodied a system on a chip (SoC), which includes all the necessary electronic a components mentioned above. The present invention uses the circuit board and components, or SoC to process any code or instructions programmed into and/or received by the entering the MEDICOBOX™ pill compliance device, and to process signals from the push button or from the reed switch in the alternative embodiment, to send one or more signals to the Bluetooth module or Wi-Fi module (which will be discussed herein later), that are in communication with the MEDICOBOX™ pill compliance device.

The microcontroller, whether on a circuit board of SoC, may be programmed by accepting code via a USB port. In other words, the microcontroller or MEDICOBOX™ pill compliance device is able to be programmed by a computer or computer server through a simple USB connection. To facilitate the USB connection, a USB compatible port can be provided a wall of the portion of the device having the electronic components therein, such as, for example, within a lower staging area underneath the pill storage compartment of the device. This is important because of the fact that it does not need additional circuits to program the device. Any errors in the device can simply be fixed by a re-insertion of the code itself. The microcontroller, whether on a circuit board of SoC, has a power input at (preferably soldered into) the circuit board, that also may operate to charge a battery. Preferably, the battery is easily replaceable and battery types can easily found in stores. Both features are important for the patient and the pharmacist because as they enable very simple troubleshooting—the inventive device simply takes one to reset the code with a USB cable to restart the device once again. At the same time, patients have the option to have rechargeable batteries, which simply need to charge for a short time before proper functionality returns. One example of a power source battery is an 1800 MaH LIPO battery, or an equivalent power source battery, which is connected to the pcb (PC board).

The second most important component of the device is the Bluetooth module. Such a module is important in communicating with the smartphone app from the device. In one embodiment, communication from the MEDICOBOX™ pill compliance device is carried out using Bluetooth, a standard for transmitting and receiving signals within short distances (10 meters). In this first embodiment, Bluetooth is preferred over other signaling types such as radio, Wi-Fi, etc., because Bluetooth is able to ease communication between the ANDROID® app and microcontroller, whether on a circuit board of SoC. Secondly, unlike Wi-Fi, Bluetooth can be used in areas where Wi-Fi is not available, and is convenient when travelling. Finally, Bluetooth is a very inexpensive form of communication—as the Bluetooth module costs approximately one dollar. The Bluetooth module itself is preferably a low-power transmitter, in which battery power is not used significantly—this allows the battery to last for a significant amount of time.

However, in a third embodiment, a reliable Wi-Fi module can be used for communication between the device and Smartphone. The Wi-Fi module preferably is a Particle Photon IoT unit Wi-Fi module or router. In a second embodiment, the Wi-Fi module or router receives a signal from the device and sends the received signal through a user computer electronically connected to the Wi-Fi module or router (for example, via the user's browser) via the Internet either directly to a Cloud storage media, or to a server that reroutes the received signal to the Cloud storage media. The user signals are privately stored in the Cloud storage media where they may be retrieved by authorized personnel, such as a patient's treating physician, also over the Internet. While not being limited, in one example, the IoT microcontroller may be an esp8266 Node MCU.

Another component of the physical device is the user activated actuator, which may be a "push button" as in FIGS. 1-10, a slidably openable lid, as in FIGS. 11-17, or a removable lid with a magnet and Reed switch 106 (or like device), as in FIG. 18 herein, where, the removable of the lid 108 causes the magnet to pass the Reed switch 106, which generates a signal (i.e., a detection of an opening or a closing), which signal then causes activation of the wireless signaling components. The push button of FIGS. 1-10 is a device component that is able to generate a digital signal when pushed. The signal is preferably stored either in a buffer or in some other type of memory storage element. In the three embodiments, the push button of FIGS. 1-10, the slidable lid of FIGS. 11-17, or the removable lid with a reed switch sensitive magnet therein, will send approximately one byte every time to the microcontroller is pressed (or otherwise actuated). Although it is very simplistic, it is key to determining whether the patient has taken the medication or not. To prevent accidental button presses, the button contains a resistor factor, which will add a certain amount of resistance when it is pressed, as is the case with a trigger on a hand gun or other firearm. Because of this, accidents such as toppling the bottle will not trigger the push button. In alternate embodiments, the digital signal activating the microcontroller and wireless communication, is caused by slidable movement of the top of the pill storage container, or by removal of a lid therefrom, to move the magnet within the lid to be out of range from the reed switch, which is then activated to generate the digital signal.

Significance:

The second version of the MEDICOBOX™ pill compliance device is also different in structure. To make the pill compliance device 10 spill-proof and child-safe, the box design also contains a key 42, 44 insertable within a slot 34 of the lid 30, which is in positional register with the corresponding slot 24 of housing 20 of the pill compliance box device 10. The locking/unlocking key 42, 44 will need to be taken out in order for the housing 20 of the pill compliance box device 10 to open for the patient to access one or more pills 27 from pill compartment 28 located within housing 20 of pill compliance box device 10. Similar to a jewelry box, this simple mechanism will prevent any form of accidental tampering or breaking of the device or its contents.

The second version of the MEDICOBOX™ pill compliance device shown in drawing FIGS. 11-17, in conclusion, has been made more compact, less expensive, and much more sturdier than the first version for a pill compliance device 1 shown in FIGS. 1-10 herein.

In the embodiment of FIG. 18, the activation is simplified by the Reed switch 106, which is sensitive to the field associated with the magnet 107, when it is moved past the Reed switch, such as when the lid is removed from the pill storage compartment of the device. As noted above, the device 100 of FIG. 18 has a hollow, bottom base portion 105 containing the reed switch 106, IoT device and other microcontroller circuitry 103 within sub-compartment 102 therein.

Medication dispenser device 100 of FIG. 18 is a tall rectangular container 101 with the electronics components 103 housed in a flat separate compartment 102 at the bottom 105 of the medication storage compartment 104. A reed switch 106 controlled by the magnet 107 attached to the cover or lid 108 is used to register a use by the patient.

Figure 20:
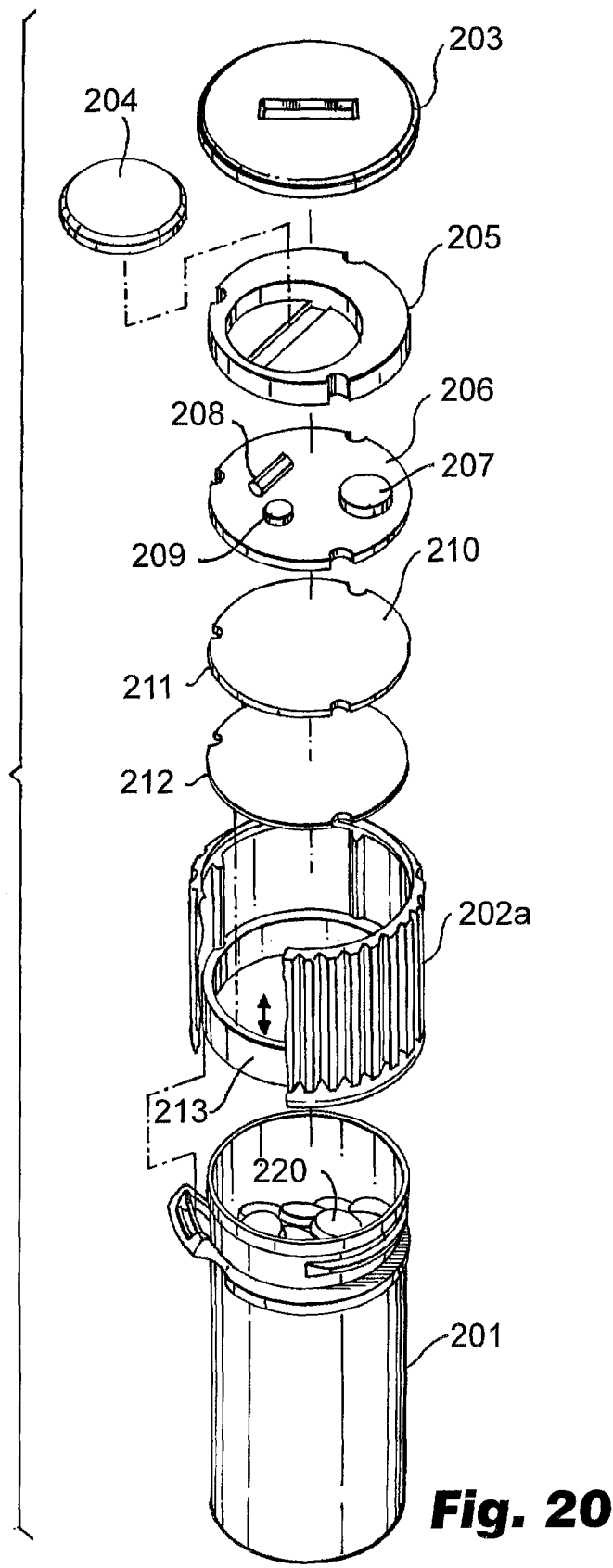
FIG. 20 is an exploded perspective view of the inventive pill compliance dispenser (bottle or device) of FIG. 19.
Figure 21:
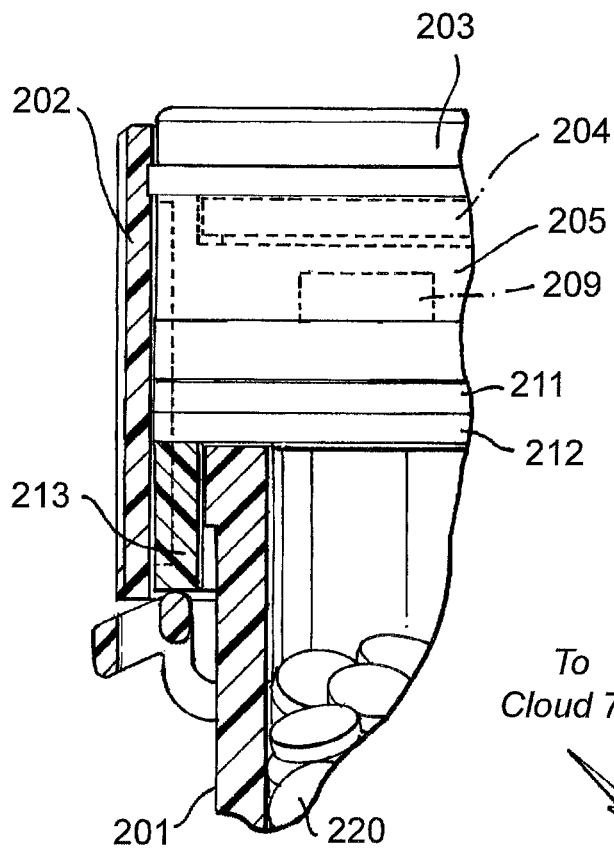
FIG. 21 is a side view detail showing cap and bottle of FIGS. 19 and 20, screwed together.
Figure 22:
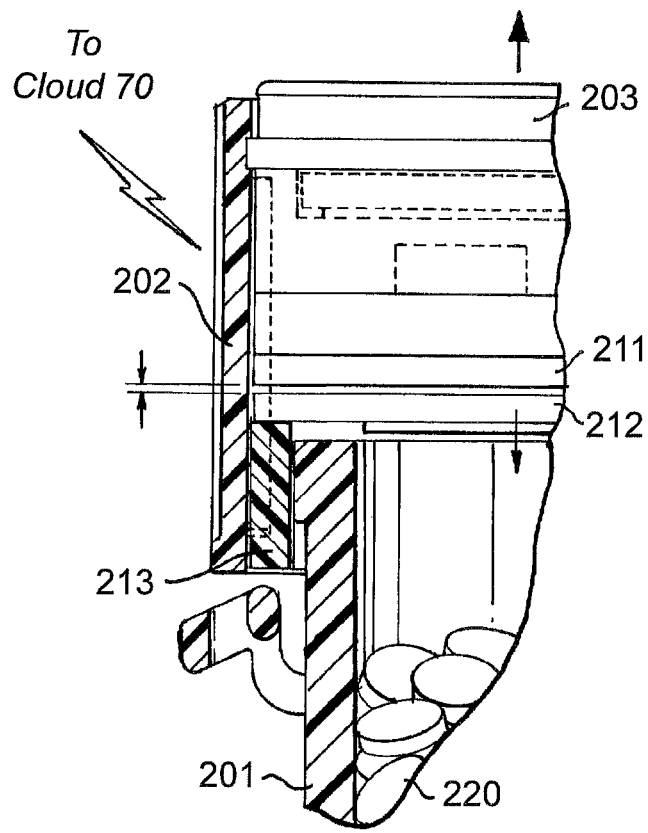
FIG. 22 is a side view detail showing the cap of FIGS. 19 and 20, highlighting removal from atop of the pill storage container or bottle.

The embodiment of FIGS. FIGS. 19-22 embodies a cylindrical container 201 with removable cap 202, or may be box-like with rectangular walls (similar in shape to medication dispenser 100 of FIG. 18,) where all of the switch and electronic components are housed in the cap 202, rather than below in a lower compartment, as in FIGS. 1-18. This "all in cap" embodiment 200, is described by FIGS. 19-22. The exploded view of FIG. 20 shows the internal parts of the cap 202 of FIG. 19. Starting at the top, a battery cover 203 is shown covering a cell 204 which may be a replaceable or rechargeable type. This is held in the battery holder 205 atop the main printed circuit board (pcb) 206 which has an ESP09 microprocessor module 207, a capacitor 208, and a resistor 209. Below that is a printed circuit board 210 supporting a capacitive touch sensor 211 which is activated by the switch press pad 212 below it as urged by the floating ring 213. provided adjacent to the cap housing 202a of the cap 202 of the pill container 201.

The ESP09 module 207 has an embedded ESP8266 processor plus wi-fi capability. A 70 ma draw from the cell 204 makes it prudent to also use the super capacitor 208 and the resistor 209 to smooth out the current in-rush with a resistor 209 while storing a charge in the capacitor 208 from the cell 204.

The PCB switch 210 is one that conducts a charge when pressed upon. When forced upwards, it will complete the circuit and then activate the printed circuit board 206. It will not generate a new charge. It is called a PCB board switch 210, but technically it does not really have its own circuit—it is just a form of switch.

There is no pushbutton on the ESP09 module 207, since the only switch is the switch PCB 210. To make the switch 210 work, the switch 210 is activated and deactivated. As a result, when the patient removes the cap 202 from the pill storage bottle 201, the movable floating ring 213 will move down, and the switch 210 will be deactivated. When put on the bottle 201, the movable floating ring 213 will be forced up, and will press upon the pcb switch 210. This will activate the electronic components of the ESP09 microprocessor module 207 which send signals to health care givers that the patient has accessed the medicine pills 220 from within the medication container 201.

The problem with the battery cell 204 is not the capacity, but the battery cell 204 does not supply the necessary current fast enough. The 70 ma draw from the circuit can take away a significant amount of load from the cell battery 204. As a result, the super-capacitor 208 is provided to accumulate the current from the battery cell 204 over a short period of time, and discharge it fast enough to power the circuit board 206. The resistor 209 is provided to control the discharge from the capacitor 208.

In the future, new alternatives to replace the GOGGLE® Sheets to a more sustainable and user friendly experience will be developed in a next version The MEDICOBOX™ pill compliance device has been tested, the tests repeated several times. Each test involved a sample size of 23 devices. To test the device code, software, etc., a device was tested 100 times (meaning that the button was pressed 200 times at different time sections), to verify whether any significant errors were made. Approximately 97 out of the possible 100 trials were successful in testing the device. This creates a 0.97 percent success rate, which falls above the 95% range. The second test done was one that tested for the maximum distance that allows the MEDICOBOX™ pill compliance device's Bluetooth® module to send a signal to the smartphone app. In such a test, the maximum distance that was attained was approximately 17.5 feet. By attaining that the average square feet in a house is approximately 1,000 square feet, assuming that the device is found in the approximate center of the house, using the formula of a hemisphere, one can find that the device coverage is approximately 1,224 feet cubed, more than enough needed for one house. At the same time, the area is also small enough to not interfere in other homes, such as apartments.

The MEDICOBOX™ pill compliance device is a very viable solution to the problem of medical noncompliance. Not only can it effectively communicate compliance information to its healthcare providers, but it can also do this in a very low price. Given that the microcontroller can be received for approximately seven dollars, the Bluetooth module can be received for approximately one dollar, and the push button, wires, etc. can all add to a negligible amount of money, one can determine a final cost of twelve dollars including the cost to 3D print the frame of the device. This cost is very affordable by the general population.

Future investigations would include creating a fingerprint-enabled device to first, prevent other users to take one's medication, an incident that is common over the recent years. By using a fingerprint, the patient is the only person who is able to open the device. Secondly, by adding a one-pill dispenser machinery, overdose is prevented. By having the device only produce one set of medication, the patient is not able to access other sets, therefore preventing unintentional and intentional overdosage.

The MEDICOBOX™ pill compliance device is able to limit noncompliance in the US healthcare. By doing this, it has the potential to save billions of dollars in wasted money, in addition to drastically increasing adherence rates. Not only will this benefit the aspect of waste from not adhering to medication, avoidable hospitalization will decrease, in addition to lowering biases in clinical trials. Finally, an increased transparency will be ensured between the doctor and the patient, which will therefore boost the treatment outcome of the patient. With broader implications, body or microbe resistance can be decreased in addition to benefits of the patient, whose in-disease activity will be decreased. By realizing the meta analysis above, it is also important for one to see the immediate need to solve the holistic waste of the healthcare system. The MEDICOBOX™ pill compliance device has this potential- to alleviate patient to doctor communications, and encourage the health regimen to allow the healthcare industry to care for our patients for today, tomorrow, and into the future.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A pill compliance device for maintaining a patient's pill supply and monitoring said patient's access to pills contained in the device to memorialize said patient's compliance with his/her pill-taking regimen, the pill compliance device comprising:
    a cylindrical container, including an inner pill or capsule storage compartment; a removable cap for covering the cylindrical container and the inner pill or capsule storage compartment of said cylindrical container;
    wherein the removable cap includes a power supply, a mechanical switch and an electronics unit, the electronics unit including a microcontroller and a memory; said mechanical switch including a capacitive touch sensor element and a switch press element communicating with a press plate;
    wherein removing the cap from the cylindrical container by said patient triggers the switch to an open switch state, generates and transfers an access signal to the microcontroller, and provides access to the pills;
    wherein placing the cap on the cylindrical container by said patient triggers the switch to a closed switch state, generates and transfers a no-access signal to the microcontroller, and prevents access to the pills;
    wherein if a no-access signal is generated within a predetermined period after an access signal is generated, the microcontroller generates a compliance notification signal that is communicated to a Wi-Fi module or router within or attached to said electronics unit and then remotely communicated wirelessly to a web-based database of a health care or medical service provider or pharmacist.

2. The pill compliance device of claim 1, wherein the Wi-Fi module or router remotely communicates the compliance notification signal to said web-based database of the health care or medical service provider or pharmacist.

3. The pill compliance device of claim 1, and wherein said press plate of said mechanical switch is in contact with the capacitive touch sensor in the closed switch state.

4. The pill compliance device of claim 1, wherein the mechanical switch further comprises a movable floating ring printed circuit board.

5. The pill compliance device of claim 1, wherein the electronics unit comprises a printed circuit board.

6. The pill compliance device as in claim 5 wherein said printed circuit board comprises an ESP09 microprocessor module, a super capacitor, and a resistor, wherein when said power supply is a battery and said battery does not supply necessary current at a fast enough speed, a draw from the circuit reduces a load from said battery, said super capacitor accumulates the current from said battery over a short period of time, and discharges the current at an increased speed to power said circuit board; and said resistor controls the discharge of the current from said super capacitor.

7. The pill compliance device of claim 1, wherein the Wi-Fi module or router directs said compliance notification signal remotely to said web-based database comprising an Internet address or URL of said health care or medical service provider or pharmacist, or to a cloud storage system, where the user data of the Wi-Fi notification signal is stored and accessed by authorized users.

8. The pill compliance device of claim 1, wherein a failure to send a Wi-Fi compliance notification signal to said health care or medical service provider or pharmacist within a "failure to take" period results in an automatic communication to notify a 3rd party that the user has failed to take a required pill or capsule.

9. The pill compliance device of claim 1, further comprising a key component for locking and unlocking said device for preventing spillage of medication and damage to said electronics unit.

10. A pill compliance device for maintaining a patient's pill supply and monitoring said patient's access to pills contained in the device to memorialize said patient's compliance with his/her pill-taking regimen, the pill compliance device comprising:
    a housing, including an inner pill or capsule storage compartment and an electronics unit;
    a removable cover covering the inner pill or capsule storage compartment of said housing, including a magnet;
    a magnetically activated switch to detect removal of said cover and magnet away from said housing, and to detect a replacement of said cover and magnet to said housing, wherein separating the magnet and cover from the magnetically activated switch triggers a transition from an active state, to a dormant state, when the magnet and switch are proximate due to the cover's presence prior to removal, and wherein attaching the cover to the housing triggers a transition from the dormant state to an active state;
    wherein a transition from the active state to the dormant state, by removing the cover from the housing generates an access signal;
    wherein a transition from the dormant state to the active state, by replacing the cover to the housing generates a pill-taken signal;
    wherein if the pill-taken signal is generated within a predetermined period after the pill-access signal is generated, the microcontroller generates a compliance notification signal that is communicated to a Wi-Fi module or router within or attached to said electronics unit, and then remotely communicated wirelessly to a web-based database of a health care or medical service provider or pharmacist to memorialize the apparent compliance.

11. The pill compliance device of claim 10, wherein the Wi-Fi module or router remotely directs the compliance notification signal to said web-based database comprising an Internet address or URL of said health care or medical service provider or pharmacist, or to a cloud storage system, where the user data of the Wi-Fi notification signal is stored and accessed by authorized users.

12. The pill compliance device of claim 10, wherein a failure to send a Wi-Fi compliance notification signal to said web-based database comprising said Internet address or URL of said health care or medical service provider or pharmacist within a "failure to take" period results in an automatic communication to notify a 3rd party that the user has failed to take a required pill or capsule.

13. The pill compliance device of claim 10, further comprising a key component for locking and unlocking said device for preventing spillage of medication and damage to said electronics unit.

14. The pill compliance device of claim 10, wherein said electronics unit is located in said removable cover.

15. The pill compliance device of claim 10, wherein said electronics unit is located in a side compartment adjacent to said inner pill or capsule storage compartment.

16. The pill compliance device of claim 10, wherein said electronics unit is located in a bottom portion of said housing adjacent to said inner pill or capsule storage compartment.

17. The pill compliance device of claim 10 in which the magnetic switch is a Reed switch.

18. The pill compliance device of claim 17, wherein the Reed switch includes a push button that overrides the signals generated by switching from a dormant to an active state or from an active to a dormant state.

19. The pill compliance device of claim 10, wherein said cover is slidably removable and replaceable.

20. The pill compliance device of claim 10, wherein said cover is unscrewed by said patient to remove the cover from the housing, and screwed down by said patient, to replace the cover to the housing.

21. A microcontroller-controlled method of providing pill compliance by use of a pill compliance device for maintaining a patient's pill supply and monitoring said patient's access to the pills contained in the device to memorialize said patient's compliance with his/her pill-taking regimen, the pill compliance device comprising an electronics unit with a microcontroller and electronic components such as memory, a housing with an inner pill or capsule storage compartment for storing pills, a removable cover covering the inner pill or capsule storage compartment of said housing, said removable cover including at least one of:
a) a magnet, a magnetically activated switch with a magnet, or,
b) a mechanical switch including a capacitive touch sensor element and a switch press element and wherein the press plate is in contact with the capacitive touch sensor in the closed switch state, each said switch is used to detect removal of said cover and magnet away from said housing, and is responsive to a replacement of said cover and magnet to said housing, wherein separating the magnet and cover from the magnetically activated switch triggers a transition from an active state, to a dormant state, when the switch is activated magnet and switch are proximate due to the cover's presence prior to removal, and wherein attaching the cover to the housing triggers a transition from the dormant state to an active state, the method including the steps of:

first generating an access signal upon removal of the removable cover from the housing and inner pill storage compartment, the access signal indicative of a transition from the active state to the dormant state;

second generating a pill-taken signal when, within a predetermined amount of time, the removable cover is replaced on the housing and inner pill storage compartment, the pill-compliance signal indicative of said patient's having ingested the pill;

in response to a pill-taken signal, the microcontroller generating a compliance notification signal and provides said compliance notification signal to a Wi-Fi module or router within, attached to or coupled to the electronic unit and then remotely communicated wirelessly to a web-based database of a health care or medical service provider or pharmacist to memorialize the apparent compliance.

* * * * *